United States Patent [19]

Kerdesky et al.

[11] Patent Number: 5,124,342
[45] Date of Patent: Jun. 23, 1992

[54] 4-HYDROXYTHIAZOLES AS 5-LIPOXYGENASE INHIBITORS

[75] Inventors: Francis A. J. Kerdesky, Grayslake; James H. Holms, Gurnee; Dee W. Brooks, Libertyville, all of Ill.

[73] Assignee: Abbott Laboratories, Abbott Park, Ill.

[21] Appl. No.: 553,836

[22] Filed: Jul. 18, 1990

Related U.S. Application Data

[63] Continuation of Ser. No. 308,177, Feb. 8, 1989, abandoned.

[51] Int. Cl.$^5$ .................. A61K 31/425; C07D 277/14; C07D 277/22
[52] U.S. Cl. ................... 514/369; 546/280; 548/182; 548/189; 548/165; 548/170
[58] Field of Search .................. 548/182, 189; 514/369

[56] References Cited

U.S. PATENT DOCUMENTS 4,935,424  6/1980  Caprathe et al. .................. 514/252

Primary Examiner—Alan L. Rotman
Attorney, Agent, or Firm—Jerry F. Janssen

[57] ABSTRACT

A composition for the inhibition of lipoxygenase enzymes comprising a pharmaceutically acceptable carrier and a compound of the formula:

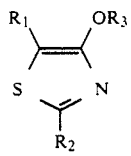

wherein
$R_1$ and $R_2$ are independently selected from the group consisting of alkyl, alkenyl, cycloalkyl, cycloalkenyl, aryl, arylalkyl, arylalkenyl, reduced heteroaryl, and reduced heteroarylalkyl and substituted derivatives thereof having one or more substituents independently selected from the group consisting of halogen, alkyl, halosubstituted alkyl, aryl, arylalkyl, reduced heteroaryl, arylalkoxy, cyano, nitro, $COR_4$, $SO_2R_4$, $NR_5R_6$, $OR_6$, $COCX_1X_2NR_6R_7$, $CON(OH)R_6$, $NR_6COR_4$, $CR_5(NH_2)CO_2R_5$, $NHCX_1X_2CO_2R_5$, $N(OH)CONR_5R_6$, $N(OH)COR_4$, $NHCONR_5R_6$, $C(NOH)NHOH$ and $CONHNR_5R_6$;

$R_3$ is selected from the group consisting of hydrogen, a pharmaceutically acceptable salt, $COR_4$, $COCX_1X_2NR_6R_7$, $CR_8R_9OR_{10}$, $CH_2CR_8(OR_{10})CH_2OR_{11}$ and $SiR_{12}R_{13}R_{14}$;

$R_4$ is selected from the group consisting of hydrogen, alkyl, alkenyl, cycloalkyl, cycloalkenyl, aryl, arylalkyl, reduced heteroaryl, reduced heteroarylalkyl, $OR_5$, $NHCX_1X_2CO_2R_5$ and $NR_6R_7$;

$R_5$ is selected from the group consisting of hydrogen, alkyl, alkenyl, cycloalkyl, aryl, arylalkyl, reduced heteroaryl, and reduced heteroarylalkyl;

$R_6$ and $R_7$ are independently selected from the group consisting of hydrogen, alkyl, alkenyl, cycloalkyl, aryl, arylalkyl, reduced heteroaryl, reduced heteroarylalkyl and $(CH_2)_nOR_5$ where n is 2–4 and $R_5$ is as defined above;

$R_8$, $R_9$, $R_{10}$ and $R_{11}$ are independently selected from the group consisting of hydrogen, alkyl, aryl, arylalkyl and $(CH_2)_nOR_5$ or at least two of $R_8$, $R_9$, $R_{10}$ and $R_{11}$ together form a ring system containing 5–10 atoms wherein said ring system is carbocyclic, heterocyclic or reduced heterocyclic and $R_5$ and n are as defined above;

$R_{12}$, $R_{13}$ and $R_{14}$ are independently selected from the group consisting of alkyl and aryl; and $X_1$ and $X_2$ are independently selected from the group consisting of hydrogen, alkyl, alkenyl, cycloalkyl, aryl, and arylalkyl; and the acid addition salts thereof.

3 Claims, No Drawings

4-HYDROXYTHIAZOLES AS 5-LIPOXYGENASE INHIBITORS

This is a continuation of application Ser. No. 07/308,177, filed Feb. 8, 1989, abandoned.

BACKGROUND OF THE INVENTION

This invention relates to compounds which inhibit lipoxygenase enzymes. It also relates to methods of inhibiting lipoxygenase enzymes in human and animal hosts in need of such treatment.

The lipoxygenases are a family of enzymes which catalyze the oxygenation of arachidonic acid. The enzyme 5-lipoxygenase converts arachidonic acid to 5-hydroperoxy-eicosatetraenoic acid (5-HPETE). This is the first step in the metabolic pathway yielding 5-hydroxyeicosatetraenoic acid (5-HETE) and the important class of potent biological mediators, the leukotrienes (LTs). Similarly 12- and 15-lipoxygenase convert arachidonic acid to 12- and 15-HPETE respectively. Biochemical reduction of 12-HPETE leads to 12-HETE, while 15-HPETE is the precursor of the class of biological agents known as the lipoxins. 12-HETE has been found in high levels in epidermal tissue of patients with psoriasis. Lipoxins have recently been shown to stimulate elastase and superoxide ion release from neutrophils.

A variety of biological effects are associated with these products from lipoxygenase metabolism of arachidonic acid and they have been implicated as mediators in various disease states. For example, the LTs $C_4$ and $D_4$ are potent constrictors of human airways in vitro and aerosol administration of these substances to non-asthmatic volunteers induces bronchoconstriction. $LTB_4$ and 5-HETE are potent chemotactic factors for inflammatory cells such as polymorphonuclear leukocytes. They also have been found in the synovial fluid of rheumatoid arthritic patients. Leukotrienes have been implicated as important mediators in asthma, allergic rhinitis, rheumatoid arthritis, psoriasis, adult respiratory distress syndrome, gout, inflammatory bowel disease, endotoxin shock, Crohn's disease, and ischemia induced myocardial injury. The biological activity of the LTs has been reviewed by Lewis and Austen, *J. Clinical Invest.* 73, 89, 1984 and by J. Sirois, *Adv. Lipid Res.*, 21, 78, (1985).

Thus, lipoxygenase enzymes are believed to play an important role in the biosynthesis of mediators of asthma, allergy, arthritis, psoriasis, and inflammation. Agents which block or modulate the activity of lipoxygenase enzymes will likely be useful in the treatment of diseases involving leukotriene pathogenesis. Some examples of 5-lipoxygenase inhibitors known to the art are: AA-861, disclosed in U.S. Pat. No. 4,393,075, issued Jul. 12, 1983, to Terro et al., pyrazolopyridines, disclosed in European Patent Application of Iriburn et al., Ser. No. 121,806, published Oct. 17, 1984; arachidonyl hydroxamic acid, disclosed in E. J. Corey et al., *J. Am. Chem. Soc.*, 106, 1503 (1984) and European Patent Application of P. H. Nelson, Ser. No. 104, 468, published Apr. 4, 1984; BW-755C, disclosed in Radmark et al., *FEBS Lett*, 110, 213, (1980); nordihydroguaiaretic acid, disclosed in Marris et al, *Prostaglandins*, 19, 371 (1980); Rev-5901, disclosed in Coutts, Meeting Abstract 70, *Prostaglandins and Leukotrienes* '84; benzoxaprofen, disclosed in J. Walker, *Pharm. Pharmacol.*, 31, 778 (1979), and hydroxamic acids, disclosed in U.S. Pat. Nos. 4,608,390 and 4,623,661, issued Aug. 16, and Nov. 18, 1986 respectively.

SUMMARY OF THE INVENTION

The compounds of this invention posses unexpected activity as inhibitors of lipoxygenase enzymes, and reduce the biosynthesis of leukotrienes $B_4$, $C_4$, $D_4$ and $E_4$. The compounds and compositions containing these compounds are useful for the treatment of disease states, in mammals, which involve leukotrienes $B_4$, $C_4$, $D_4$ and $E_4$.

The compounds of this invention are of the formula:

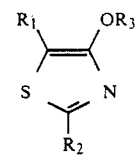

wherein $R_1$ is selected from the group consisting of aryl and substituted derivatives thereof with one or more substituents independently selected from the group consisting of halogen, alkyl, halosubstituted alkyl, aryl, arylalkyl, reduced heteroaryl, arylalkoxy, cyano, nitro, $COR_4$, $SO_2R_4$, $NR_3R_6$, $OR_6$, $COCX_1X_2NR_6R_7$, $CON(OH)R_6$, $NR_6COR_4$, $CR_5(NH_2)CO_2R_5$, $NHCX_1X_2CO_2R_5$, $N(OH)CONR_5R_6$, $N(OH)COR_4$, $NHCONR_5R_6$, $C(NOH)NHOH$ and $CONHNR_5R_6$;

$R_2$ is selected from the group consisting of aryl, substituted derivatives thereof and substituted alkyl with one or more substituents independently selected from the group consisting of halogen, alkyl, halosubstituted alkyl, aryl, arylalkyl, reduced heteroaryl, arylalkoxy, cyano, nitro, $COR_4$, $SO_2R_4$, $NR_3R_6$, $OR_6$, $COCX_1X_2NR_6R_7$, $CON(OH)R_6$, $NR_6COR_4$, $CR_5(NH_2)CO_2R_5$, $NHCX_1X_2CO_2R_5$, $N(OH)CONR_5R_6$, $N(OH)COR_4$, $NHCONR_5R_6$, $C(NOH)NHOH$ and $CONHNR_5R_6$; and arylalkyl and substituted derivatives thereof with one or more substituents independently selected from the group consisting of halogen, alkyl, halosubstituted alkyl, cyano, nitro, $COR_4$, $SO_2R_4$, $NR_5R_6$ and $OR_6$;

$R_3$ is selected from the group consisting of hydrogen, a pharmaceutically acceptable salt, $COR_4$, $COCX_1X_2NR_6R_7$, $CR_8R_9OR_{10}$, $CH_2CR_8(OR_{10})CH_2OR_{11}$ and $SiR_{12}R_{13}R_{14}$ $R_4$ is selected from the group consisting of hydrogen, alkyl, alkenyl, cycloalkyl, cycloalkenyl, aryl, arylalkyl, reduced heteroaryl, reduced heteroarylalkyl, $OR_5$, $NHCX_1X_2CO_2R_5$ and $NR_6R_7$;

$R_5$ is selected from the group consisting of hydrogen, alkyl, alkenyl, cycloalkyl, aryl, arylalkyl, reduced heteroaryl, and reduced heteroarylalkyl;

$R_6$ and $R_7$ are independently selected from the group consisting of hydrogen, alkyl, alkenyl, cycloalkyl, aryl, arylalkyl, reduced heteroaryl, reduced heteroarylalkyl and $(CH_2)_nOR_5$ where n is 2-4 and $R_5$ is as defined above;

$R_8$, $R_9$, $R_{10}$ and $R_{11}$ are independently selected from the group consisting of hydrogen, alkyl, aryl, arylalkyl and $(CH_2)_nOR_5$ or at least two of $R_8$, $R_9$, $R_{10}$ and $R_{11}$ together form a ring system containing 5–10 atoms wherein said ring system is carbocyclic, heterocyclic or reduced heterocyclic and $R_5$ and n are as defined above;

$R_{12}$, $R_{13}$ and $R_{14}$ are independently selected from the group consisting of alkyl and aryl; and $X_1$ and $X_2$ are independently selected from the group consisting of hydrogen, alkyl, alkenyl, cycloalkyl, aryl, and arylalkyl; provided that when $R_1$ is phenyl or substituted phenyl $R_2$ cannot be substituted alkyl, when $R_1$ is aryl or substituted aryl $R_2$ cannot be phenyl, substituted phenyl, $CH(C_6H_5)_2$, $CH(C_6H_5)CO_2Et$ or 2-methylindole and when $R_3$ is $SiR_{12}R_{13}R_{14}$, $R_1$ and $R_2$ cannot both be unsubstituted phenyl; and the acid addition salts thereof.

This invention also relates to pharmaceutical compositions and a method of inhibiting lipoxygenase enzymes and related disorders comprising the administration to a host in need of such treatment of a compound of the formula:

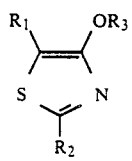
II wherein $R_1$ and $R_2$ are independently selected from the group consisting of alkyl, alkenyl, cycloalkyl, cycloalkenyl, aryl, arylalkyl, arylalkenyl, reduced heteroaryl, and reduced heteroarylalkyl and substituted derivatives thereof having one or more substituents independently selected from the group consisting of halogen, alkyl, halosubstituted alkyl, aryl, arylalkyl, reduced heteroaryl, arylalkoxy, cyano, nitro, $COR_4$, $SO_2R_4$, $NR_5R_6$, $OR_6$, $COCX_1X_2NR_6R_7$, $CON(OH)R_6$, $NR_6COR_4$, $CR_5(NH_2)CO_2R_5$, $NHCX_1X_2CO_2R_5$, $N(OH)CONR_5R_6$, $N(OH)COR_4$, $NHCONR_5R_6$, $C(NOH)NHOH$ and $CONHNR_5R_6$;

$R_3$ is selected from the group consisting of hydrogen, a pharmaceutically acceptable salt, $COR_4$, $COCX_1X_2NR_6R_7$, $CR_8R_9OR_{10}$, $CH_2CR_8(OR_{10})CH_2OR_{11}$ and $SiR_{12}R_{13}R_{14}$;

$R_4$ is selected from the group consisting of hydrogen, alkyl, alkenyl, cycloalkyl, cycloalkenyl, aryl, arylalkyl, reduced heteroaryl, reduced heteroarylalkyl, $OR_5$, $NHCX_1X_2CO_2R_5$ and $NR_6R_7$;

$R_5$ is selected from the group consisting of hydrogen, alkyl, alkenyl, cycloalkyl, aryl, arylalkyl, reduced heteroaryl, and reduced heteroarylalkyl;

$R_6$ and $R_7$ are independently selected from the group consisting of hydrogen, alkyl, alkenyl, cycloalkyl, aryl, arylalkyl, reduced heteroaryl, reduced heteroarylalkyl and $(CH_2)_nOR_5$ where n is 2-4 and $R_5$ is as defined above;

$R_8$, $R_9$, $R_{10}$ and $R_{11}$ are independently selected from the group consisting of hydrogen, alkyl, aryl, arylalkyl and $(CH_2)_nOR_5$ or at least two of $R_8$, $R_9$, $R_{10}$ and $R_{11}$ together form a ring system containing 5-10 atoms wherein said ring system is carbocyclic, heterocyclic or reduced heterocyclic and $R_5$ and n are as defined above;

$R_{12}$, $R_{13}$ and $R_{14}$ are independently selected from the group consisting of alkyl and aryl; and $X_1$ and $X_2$ are independently selected from the group consisting of hydrogen, alkyl, alkenyl, cycloalkyl, aryl, and arylalkyl; and the acid addition salts thereof.

DETAILED DESCRIPTION OF THE INVENTION

The present invention provides for compounds which exhibit unexpected activity for lipoxygenase enzyme inhibition, particularly, 5-lipoxygenase, and thereby reduce the biosynthesis of leukotrienes $B_4$, $C_4$, $D_4$, and $E_4$.

The novel compounds of this invention are those of the formula:

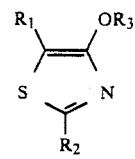
I wherein $R_1$ is selected from the group consisting of aryl and substituted derivatives thereof with one or more substituents independently selected from the group consisting of halogen, alkyl, halosubstituted alkyl, aryl, arylalkyl, reduced heteroaryl, arylalkoxy, cyano, nitro, $COR_4$, $SO_2R_4$, $NR_3R_6$, $OR_6$, $COCX_1X_2NR_6R_7$, $CON(OH)R_6$, $NR_6COR_4$, $CR_5(NH_2)CO_2R_5$, $NHCX_1X_2CO_2R_5$, $N(OH)CONR_5R_6$, $N(OH)COR_4$, $NHCONR_5R_6$, $C(NOH)NHOH$ and $CONHNR_5R_6$;

$R_2$ is selected from the group consisting of aryl, substituted derivatives thereof and substituted alkyl with one or more substituents independently selected from the group consisting of halogen, alkyl, halosubstituted alkyl, aryl, arylalkyl, reduced heteroaryl, arylalkoxy, cyano, nitro, $COR_4$, $SO_2R_4$, $NR_3R_6$, $OR_6$, $COCX_1X_2NR_6R_7$, $CON(OH)R_6$, $NR_6COR_4$, $CR_5(NH_2)CO_2R_5$, $NHCX_1X_2CO_2R_5$, $N(OH)CONR_5R_6$, $N(OH)COR_4$, $NHCONR_5R_6$, $C(NOH)NHOH$ and $CONHNR_5R_6$; and arylalkyl and substituted derivatives thereof with one or more substituents independently selected from the group consisting of halogen, alkyl, halosubstituted alkyl, cyano, nitro, $COR_4$, $SO_2R_4$, $NR_5R_6$ and $OR_6$;

$R_3$ is selected from the group consisting of hydrogen, a pharmaceutically acceptable salt, $COR_4$, $COCX_1X_2NR_6R_7$, $CR_8R_9OR_{10}$, $CH_2CR_8(OR_{10})CH_2OR_{11}$ and $SiR_{12}R_{13}R_{14}$ $R_4$ is selected from the group consisting of hydrogen, alkyl, alkenyl, cycloalkyl, cycloalkenyl, aryl, arylalkyl, reduced heteroaryl, reduced heteroarylalkyl, $OR_5$, $NHCX_1X_2CO_2R_5$ and $NR_6R_7$;

$R_5$ is selected from the group consisting of hydrogen, alkyl, alkenyl, cycloalkyl, aryl, arylalkyl, reduced heteroaryl, and reduced heteroarylalkyl;

$R_6$ and $R_7$ are indendently selected from the group consisting of hydrogen, alkyl, alkenyl, cycloalkyl, aryl, arylalkyl, reduced heteroaryl, reduced heteroarylalkyl and $(CH_2)_nOR_5$ where n is 2-4 and $R_5$ is as defined above;

$R_8$, $R_9$, $R_{10}$ and $R_{11}$ are independently selected from the group consisting of hydrogen, alkyl, aryl, arylalkyl and $(CH_2)_nOR_5$ or at least two of $R_8$, $R_9$, $R_{10}$ and $R_{11}$ together form a ring system containing 5-10 atoms wherein said ring system is carbocyclic, heterocyclic or reduced heterocyclic and $R_5$ and n are as defined above;

$R_{12}$, $R_{13}$ and $R_{14}$ are independently selected from the group consisting of alkyl and aryl; and $X_1$ and $X_2$ are independently selected from the group consisting of hydrogen, alkyl, alkenyl, cycloalkyl, aryl, and arylalkyl; provided that when $R_1$ is phenyl or substituted phenyl $R_2$ cannot be substituted alkyl, when $R_1$ is aryl or substituted aryl $R_2$ cannot be phenyl, substituted phenyl, $CH(C_6H_5)_2$, $CH(C_6H_5)CO_2$ Et or 2-methylindole and when $R_3$ is $SiR_{12}R_{13}R_{14}$, $R_1$ and $R_2$ cannot both be unsubstituted phenyl; and the acid addition salts thereof.

The compounds useful in the method of treatment for inhibition of lipoxygenase enzymes are of the following formula:

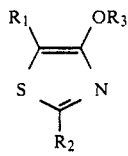

II wherein $R_1$ and $R_2$ are independently selected from the group consisting of alkyl, alkenyl, cycloalkyl, cycloalkenyl, aryl, arylalkyl, arylalkenyl, reduced heteroaryl, and reduced heteroarylalkyl and substituted derivatives thereof having one or more substituents independently selected from the group consisting of halogen, alkyl, halosubstituted alkyl, aryl, arylalkyl, reduced heteroaryl, arylalkoxy, cyano, nitro, $COR_4$, $SO_2R_4$, $NR_5R_6$, $OR_6$, $COCX_1X_2NR_6R_7$, $CON(OH)R_6$, $NR_6COR_4$, $CR_5(NH_2)CO_2R_5$, $NHCX_1X_2CO_2R_5$, $N(OH)CONR_5R_6$, $N(OH)COR_4$, $NHCONR_5R_6$, $C(NOH)NHOH$ and $CONHNR_5R_6$;

$R_3$ is selected from the group consisting of hydrogen, a pharmaceutically acceptable salt, $COR_4$, $COCX_1X_2NR_6R_7$, $CR_8R_9OR_{10}$, $CH_2CR_8(OR_{10})CH_2OR_{11}$ and $SiR_{12}R_{13}R_{14}$;

$R_4$ is selected from the group consisting of hydrogen, alkyl, alkenyl, cycloalkyl, cycloalkenyl, aryl, arylalkyl, reduced heteroaryl, reduced heteroarylalkyl, $OR_5$, $NHCX_1X_2CO_2R_5$ and $NR_6R_7$;

$R_5$ is selected from the group consisting of hydrogen, alkyl, alkenyl, cycloalkyl, aryl, arylalkyl, reduced heteroaryl, and reduced heteroarylalkyl;

$R_6$ and $R_7$ are independently selected from the group consisting of hydrogen, alkyl, alkenyl, cycloalkyl, aryl, arylalkyl, reduced heteroaryl, reduced heteroarylalkyl and $(CH_2)_nOR_5$ where n is 2-4 and $R_5$ is as defined above;

$R_8$, $R_9$, $R_{10}$ and $R_{11}$ are independently selected from the group consisting of hydrogen, alkyl, aryl, arylalkyl and $(CH_2)_nOR_5$ or at least two of $R_8$, $R_9$, $R_{10}$ and $R_{11}$ together form a ring system containing 5-10 atoms wherein said ring system is carbocyclic, heterocyclic or reduced heterocyclic and $R_5$ and n are as defined above;

$R_{12}$, $R_{13}$ and $R_{14}$ are independently selected from the group consisting of alkyl and aryl; and $X_1$ and $X_2$ are independently selected from the group consisting of hydrogen, alkyl, alkenyl, cycloalkyl, aryl, and arylalkyl; and the acid addition salts thereof.

The compounds of Formula II may also be substituted with one or more substituents as noted above for the compounds of Formula I.

Pharmaceutical compositions which contain compounds of Formula I and a pharmaceutically acceptable carrier are also part of this invention.

Preferred compounds of Formula II that are useful for the inhibition of lipoxygenase enzymes are those where $R_1$ is aryl, alkyl, or substituted aryl and alkyl, $R_2$ is aryl or substituted aryl, and $R_3$ is hydrogen, acyl or a pharmaceutically acceptable salt. Also preferred are those compounds where $R_1$ is aryl or substituted aryl, $R_2$ is a substituted alkyl or substituted arylalkyl, and $R_3$ is hydrogen, acyl or a pharmaceutically acceptable salt. Most preferred are those compounds where $R_1$ is aryl or substituted aryl and $R_2$ is aryl or substituted aryl, and $R_3$ is hydrogen, acyl, or a pharmaceutically acceptable salt.

The term "alkyl" as used herein refers to straight and branched chain radicals having 1 to 12 carbon atoms which may be optionally substituted as herein defined above. Representative of such radicals are methyl, ethyl, n-propyl, isopropyl, n-butyl, sec-butyl, isobutyl, tert-butyl, and the like.

The term "alkenyl" as used herein refers to straight and branched chain unsaturated radicals having 2 to 12 carbon atoms, which may be optionally substituted as defined above. Representative of such groups are ethenyl, 1-propenyl, 2-propenyl, 2-methyl-1-propenyl, 1-butenyl, 2-butenyl, and the like.

The term "carbocyclic" as used herein refers to a monocyclic or polycyclic hydrocarbon containing fused or non-fused ring system which may be optionally substituted as defined above. Representative of such groups are cyclopentyl, cyclohexyl, 2-cyclohexenyl, tetrahydronaphthalene.

Representative examples of the $CR_8R_9OR_{10}$ radical are 1-methoxy cyclohexane, 2-Hydroxy-pyrrol, 1-Methyl-tetrahydrofuran, 2-Oxazole and 1, 2, 4-Oxadiazole.

The terms "cycloalkyl" and "cycloalkenyl" as used herein refer to saturated and unsaturated cyclic or bicyclic radicals having 3 to 12 carbon atoms which may be optionally substituted as defined above. Representative of such groups are cyclopropyl, cyclobutyl, cyclopentyl, cyclohexyl, norbornyl, 2-chlorocyclohexyl, and the like.

The term "aryl" as used herein refers to mono or polycyclic hydrocarbon group containing fused or non-fused aromatic ring systems which may contain one or more hetero atoms such as O, N or S in the ring system and which may be optionally substituted as defined herein. Representative of such groups are phenyl, naphthyl, biphenyl, triphenyl, pyridinyl, pyrrolyl, pyrimidinyl, furyl, thienyl, indolyl, pyrazinyl, isoquinolyl, benzopyranyl, benzofuryl, benzothiophenyl, imidazolyl, carbazolyl, and the like.

The term "aroyl" as used herein refers to the radical aryl-CO— wherein the aryl ring may be optionally substituted as herein before defined.

The term "reduced heteroaryl" as used herein refers to a mono- or polycyclic group comprising fused or non-fused ring systems which contain at least one ring which is non-aromatic in character. The ring system may be fully or partially saturated, may contain one or more heteroatoms such as O, N, or S and may be optionally substituted as herein before defined. Representative of such ring systems are tetrahydrofuran, dihydropyran, indane, 2,3-dihydrobenzofuran, piperidine, indane, piperidine, and the like.

The term "alkoxy" as used herein refers to straight and branched chain oxygen ether radicals having 1 to 12 carbon atoms which may be optionally substituted. Representative of such groups are methoxy, ethoxy, isopropoxy, n-butoxy, sec-butoxy, isobutoxy, tert-butoxy, and the like.

The term "aryloxy" as used herein refers to substituted or unsubstituted aryl ethers which may be optionally substituted as herein before defined. Representative of such groups are 4-acetylphenoxy, phenoxy, 1-naphthoxy, 2-naphthoxy, and the like.

The terms "halo" and "halogen" as used herein refer to radicals derived from the elements fluorine, chlorine, bromine and iodine.

The term "halo-substituted" alkyl, alkenyl or alkinyl refers to a radical as described above substituted with one or more halogens, and which may also be additionally substituted as defined above. Representatives of such groups are chloromethyl, trifluoromethyl, 2,2,2-trichloroethyl, 2,2-dichloro, 1-hydroxybutyl, and the like.

All of the alkyl, alkenyl, alkinyl, cycloalkyl, cycloalkenyl, aryl, arylalkyl, reduced heteroaryl, reduced heteroarylalkyl, $X_1$ and $X_2$ radicals may in turn be substituted with various groups as defined above. Representatives of this group are 2-chlorophenyl-1-naphthyl, 2,4-dichlorophenyl-4-benzyl and 2-fluoromethyl-cyclohexyl-methyl.

The term "pharmaceutically acceptable salts" refers to the relatively non-toxic, inorganic or organic acid addition salts and alkaline earth metal salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, lauryl sulphate, and the like. Representative alkali or alkaline earth metal sales include sodium, calcium, potassium and magnesium salts, and the like. It will be apparent to those skilled in the art that, depending upon the number of available amino groups for salt formation, the salts of this invention can be per-N-salts.

Certain compounds of this invention may exist in optically active forms. The R and S isomers and mixtures thereof, including racemic mixtures as well as the cis and trans mixtures are contemplated by this invention. Additional assymetric carbon atoms may be present in a substituent group such as an alkyl group. All such isomers as well as the mixtures thereof are intended to be included in the invention.

The present invention includes one or more of the compounds of Formula II formulated into compositions together with one or more non-toxic pharmaceutically acceptable carriers, adjuvants or vehicles which are collectively referred to herein as carriers, for parenteral injection, for oral administration in solid or liquid form, for rectal administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the abovementioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include powders, sprays and inhalants. The active component is admixed under sterile conditions with a pharmaceutically acceptable carrier and any needed preservatives, buffers or propellants as may be required. Opthalmic formulations, eye ointments, powders and solutions are also contemplated as being within the scope of this invention.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Representative Compounds of Formula I and Formula II are shown in Table I.

TABLE I

| Compound | $R_1$ | $R_2$ | $R_3$ |
|---|---|---|---|
| 1 | methyl | 2-pyridyl | H |
| 2 | methyl | 3-pyridyl | H |
| 3 | methyl | 4-pyridyl | H |
| 4 | methyl | 3-quinolinyl | H |
| 5 | methyl | 2-furanyl | H |
| 6 | methyl | 2-(6-methoxybenzothiazolyl) | H |
| 7 | methyl | 2-thiophenyl | H |
| 8 | methyl | 4-pyrazolyl | H |
| 9 | methyl | 4-fluorophenyl | H |
| 10 | methyl | 4-bromophenyl | H |
| 11 | methyl | 4-chlorophenyl | H |
| 12 | methyl | 4-nitrophenyl | H |
| 13 | methyl | 4-$C_6H_4$—$CO_2CH_2CH_2C_6H_5$ | H |
| 14 | methyl | 4-$C_6H_4$—$CONH_2$ | H |
| 15 | methyl | 4-$C_6H_4$—$C_6H_5$ | H |
| 16 | methyl | 4-$C_6H_4$—$CF_3$ | H |
| 17 | methyl | 4-$C_6H_4$—$CO_2CH_3$ | H |
| 18 | methyl | 4-$C_6H_4$—$COCH_3$ | H |
| 19 | methyl | 4-$C_6H_4$—$CO_2H$ | H |
| 20 | methyl | 4-$C_6H_4$—CN | H |
| 21 | methyl | 4-$C_6H_4$—$CSNH_2$ | H |
| 22 | methyl | 4-$C_6H_4$—$SCF_3$ | H |
| 23 | methyl | 4-$C_6H_4$—$CO_2CH_2CH_3$ | H |
| 24 | methyl | 2-fluorophenyl | H |
| 25 | methyl | 3-fluorophenyl | H |
| 26 | methyl | 3-bromophenyl | H |
| 27 | methyl | 3,5-bis-trifluoromethylphenyl | H |
| 28 | methyl | 3,5-dinitrophenyl | H |
| 29 | methyl | 2-chloro-3-methylphenyl | H |
| 30 | phenyl | 4-$C_6H_4$—$CO_2H$ | H |
| 31 | methyl | phenyl | H |
| 32 | methyl | 4-methoxyphenyl | H |
| 33 | methyl | 4-methylphenyl | H |
| 34 | phenyl | phenyl | H |
| 35 | —$CH_2CH_3$ | phenyl | H |
| 36 | —$(CH_2)_2CH_3$ | phenyl | H |
| 37 | —$(CH_2)_3CH_3$ | phenyl | H |
| 38 | —$(CH_2)_2C_6H_5$ | phenyl | H |
| 39 | —$CH_2CO_2CH_3$ | phenyl | H |
| 40 | —$CH_2CON(OH)CH_3$ | phenyl | H |
| 41 | phenyl | 3-pyridyl | H |

TABLE I-continued

| Compound | $R_1$ | $R_2$ | $R_3$ |
|---|---|---|---|
| 42 | phenyl | 4-pyridyl | H |
| 43 | phenyl | 4-methoxyphenyl | H |
| 44 | phenyl | 4-biphenyl | H |
| 45 | phenyl | methyl | H |
| 46 | phenyl | 4-methylphenyl | H |
| 47 | phenyl | 4-fluorophenyl | H |
| 48 | phenyl | 4-ethoxyphenyl | H |
| 49 | phenyl | $-(CH_2)_4CH_3$ | H |
| 50 | phenyl | phenyl | $-OCCH_3$ |
| 51 | phenyl | phenyl | $-OC(CH_2)_4CH_3$ |
| 52 | phenyl | phenyl | $-CO(CH_3)_3$ |
| 53 | phenyl | phenyl | $-CO(CH_2)_2CO_2CH_2CH_3$ |
| 54 | $-(CH_2)_2CH_3$ | phenyl | $-COOCH_2CH_3$ |
| 55 | $-(CH_2)_2CH_3$ | phenyl | $-CONHCH_2$ |
| 56 | $-(CH_2)_2CH_3$ | phenyl | $-COC_6H_5$ |
| 57 | $-(CH_2)_2CH_3$ | phenyl | $-CONHC(CH_3)_3$ |
| 58 | $-(CH_2)_2CH_3$ | phenyl | $-CONHC_6H_5$ |
| 59 | $-(CH_2)_2CH_3$ | phenyl | $-COCH_3$ |
| 60 | methyl | $4-C_6H_4-CO_2CH_3$ | $-COCH_3$ |
| 61 | methyl | 6-methoxybenzothiazoyl | $-COCH_3$ |
| 62 | phenyl | 4-methylphenyl | $-COCH_3$ |
| 63 | phenyl | 4-ethoxyphenyl | $-COCH_3$ |
| 64 | methyl | $4-C_6H_4-CO_2(CH_2)_2-C_6H_5$ | $-COCH_3$ |
| 66 | methyl | $4-C_6H_4-CO_2H$ | $-COCH_3$ |
| 67 | $(CH_2)_3CH_3$ | phenyl | $-COCH_3$ |
| 68 | $(CH_2)_2CH_3$ | $(CH_2)_4CH_3$ | $-COCH_3$ |

Other representative compounds which are useful in the methods of this invention for the inhibition of lipoxygenase enzymes are shown in Table II below.

TABLE II

| $R_1$ | $R_2$ | $R_3$ |
|---|---|---|
| methyl | benzyl | H |
| 4-methylphenyl | 4-chlorophenyl | H |
| $CO_2CH_2CH_3$ | 2-furanyl | H |
| phenyl | 4-chlorophenyl | H |
| 4-methylphenyl | phenyl | H |
| methyl | 6-methylbenzothiazole | H |
| methyl | benzothiazole | H |
| methyl | 2-methyl-naphtho[2,1-d]thiazole | H |
| $3-C_6H_4-NHCOCH_3$ | phenyl | H |
| 2-phenyl-benzothiazol-like | phenyl | H |
| $4-C_6H_4-COCH_3$ | methyl | H |
| 4-nitrophenyl | methyl | H |
| 4-chlorophenyl | methyl | H |
| $-(CH_2)_2CH_3$ | 2,6-dichlorophenyl | H |
| $-(CH_2)_3CH_3$ | 2,6-dichlorophenyl | H |
| $-CH_2CO_2CH_2CH_3$ | 2,6-dichlorophenyl | H |
| methyl | 2-benzimidazolyl | H |
| methyl | 2-benzothiazole | H |
| methyl | 5-hydroxy-2-benzothiazole | H |
| methyl | 2-naphthylthiazole | H |
| methyl | 1-piperidinyl | H |
| phenyl | 1-piperidinyl | H |
| 4-methylphenyl | 1-piperidinyl | H |
| phenyl | 4-methyl-1-piperidinyl | H |
| 4-isopropylphenyl | 4-methyl-1-piperidinyl | H |
| 4-methoxyphenyl | 4-methyl-1-piperidinyl | H |
| 4-fluorophenyl | 4-methyl-1-piperidinyl | H |
| 2-chlorophenyl | 4-methyl-1-piperidinyl | H |
| phenyl | 4-propyl-1-piperidinyl | H |
| phenyl | 4-(2-propene)-1-piperidinyl | H |

TABLE II-continued

| R₁ | R₂ | R₃ |
|---|---|---|
| phenyl | 4-(2-hydroxypropyl)-1-piperidinyl | H |
| 4-fluorophenyl | -N⟨piperidinyl⟩-C₆H₄-CH₃ (4-(4-methylphenyl)-1-piperidinyl) | H |
| 4-fluorophenyl | 4-morpholinyl N-oxide | H |
| methyl | 2-methyl-4-hydroxy-5-methyl-thiazolyl (enol form) | H |
| 2-quinolinyl | phenyl | H |
| 4-methyl-2-quinolinyl | phenyl | H |
| 4-methoxy-2-quinolinyl | phenyl | H |
| 3-bromo-2-quinolinyl | phenyl | H |
| 1-isoquinolinyl | phenyl | H |
| 2-(1-hydroxyethylidene)-3-ethylidene-thiazoline (see structure) | methyl | H |
| 4-fluorophenyl | 1-pyrrolidinyl | H |
| 4-methylphenyl | 4-methyl-1-piperidinyl | H |
| phenyl | CH₂CON(piperidinyl) | H |
| phenyl | CH₂CON(morpholinyl) | H |
| phenyl | CH₂CONH₂ | H |
| phenyl | CH₂SO₂C₆H₅ | H |
| phenyl | CH₂COC₆H₅ | H |
| phenyl | CH(C₆H₅)₂ | H |
| phenyl | CH₂-(indolinyl/dihydroindole) | H |
| phenyl | CH₂CN | H |
| phenyl | CH(C₆H₅)CO₂CH₂CH₃ | H |
| phenyl | 2-chlorophenyl | —COCH₃ |
| phenyl | phenyl | —COCH₃ |
| phenyl | 4-chlorophenyl | —COCH₃ |
| 4-methylphenyl | phenyl | —COCH₃ |
| CO₂CH₂CH₃ | 2-furanyl | COC₆H₅ |
| CO₂CH₂CH₃ | phenyl | COC₆H₅ |
| 4-methylphenyl | 4-chlorophenyl | —COCH₃ |
| 4-chlorophenyl | phenyl | —COCH₃ |
| methyl | 4-acetyl-5-methyl-2-thiazole | —COCH₃ |
| methyl | 4-pyridyl | —CH₂CHOHCH₂NHC(CH₃)₃ |
| phenyl | methyl | —COCH₃ |
| methyl | (CH₂)₂CH₂OH | H |
| methyl | (CH₂)₂CHOHCH₃ | H |
| phenyl | CH₂CH₂OH | H |
| phenyl | CH₂OH | H |
| phenyl | CH₂OCH₂CH₃ | H |
| methyl | CH₂OCH₂CH₂OCH₃ | H |
| methyl | (CH₂)₂C₆H₅ | H |
| methyl | CH(CH₃)C₆H₅ | H |

TABLE II-continued

| $R_1$ | $R_2$ | $R_3$ |
|---|---|---|
| methyl | 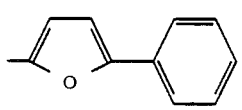 | H |
| phenyl |  | H |
| methyl | 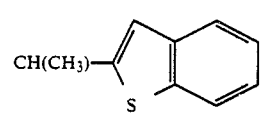 | H |
| methyl | 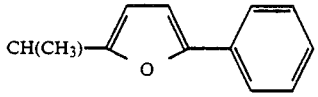 | H |
| methyl | 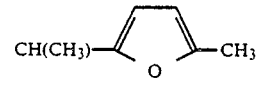 | H |
| phenyl | 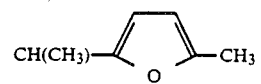 | H |
| methyl | $(CH_2)_2CH_2NH_2$ | H |
| methyl | $(CH_2)_2CH_2N(CH_2CH_3)_2$ | H |
| methyl | $(CH_2)_3CH(NH_2)CO_2H$ | H |
| phenyl | $(CH_2)_3CH(NH_2)CO_2H$ | H |
| phenyl | $CH_2CHNH_2CO_2H$ | H |
| methyl | $(CH_2)_3C(CH_3)(NH_2)CO_2H$ | H |
| phenyl | $CH_2C(CH_3)(NH_2)CO_2H$ | H |
| methyl | $4\text{-}C_6H_4\text{-}CH_2NH_2$ | H |
| methyl | $CH{=}CH\text{-}CH_2N(CH_2CH_3)_2$ | H |
| methyl | 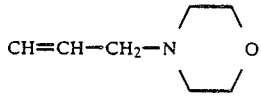 | H |
| methyl | $(CH_2)_3NHCONH_2$ | H |
| methyl | $CH(CH_3)NHCONH_2$ | H |
| methyl | $CH(CH_3)N(OH)CONH_2$ | H |
| methyl | $CH(CH_3)N(OH)COCH_3$ | H |
| methyl | $CH(CH_3)C(NOH)NHOH$ | H |
| methyl | $CH(CH_3)CONHNH_2$ | H |
| methyl | $CH(CH_3)CONHNHC_6H_5$ | H |
| methyl | $CH(CH_3)CON(OH)CH_3$ | H |
| phenyl | $CH(CH_3)CON(OH)CH_3$ | H |
| phenyl | $CH(CH_3)N(OH)CONH_2$ | H |
| phenyl | 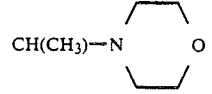 | H |
| methyl | $(CH_2)_3NHCH_2CO_2CH_3$ | H |
| methyl | 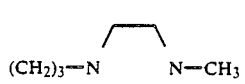 | H |
| methyl | $4\text{-}C_6H_4\text{-}CH(NH_2)CO_2H$ | H |
| methyl | $4\text{-}C_6H_4\text{-}CHNHCONH_2$ | H |
| methyl | $4\text{-}C_6H_4\text{-}CH(CH_3)\text{-}NHCONH_2$ | H |
| methyl | $4\text{-}C_6H_4\text{-}CH(CH_3)\text{-}N(OH)CONH_2$ | H |

TABLE II-continued

| R₁ | R₂ | R₃ |
|---|---|---|
| methyl | 4-C₆H₄—CH(CH₃)—N(OH)COCH₃ | H |
| methyl | 4-C₆H₄—CONHCH₂CH₂N(CH₂CH₃)₂ | H |
| methyl | 4-C₆H₄—CONHCH(CH₃)CO₂H | H |
| methyl | 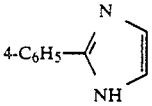 | H |
| methyl | 2-benzofuranyl | H |
| methyl | 1-methyl-2-indolyl | H |
| methyl | 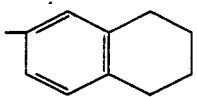 | H |
| methyl | 2-benzoxazole | H |
| phenyl | 5-methyl-2-thiophenyl | H |
| phenyl | 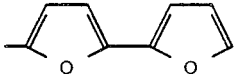 | H |
| methyl | 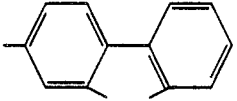 | H |
| phenyl | phenyl | —CH₂OCH₂CH₂OCH₃ |
| phenyl | phenyl | —COCH₂NH₂ |
| phenyl | methyl | —COCH(CH₃)NH₂ |
| methyl | phenyl | —COCH(C₆H₅)NH₂ |
| phenyl | CH₂CH(NCOCH₃)CO₂CH₃ | —COCH₃ |
| methyl | phenyl | —CH₂N(CH₂CH₃)₂ |
| methyl | phenyl | —CH(CH₃)OCH₃ |
| phenyl | phenyl | 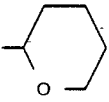 |
| phenyl | phenyl | —Si(CH₃)₂C₆H₅ |
| phenyl | phenyl | —Si(CH₃)₂C(CH₃)₃ |
| phenyl | phenyl | —CH₂CHOHCH₂OH |
| phenyl | phenyl | 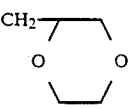 |

The compounds of Table II and many other compounds having lipoxygenase inhibiting activity are included in Formula II. While many of these compounds are old and are disclosed in the following list of reference, none are taught to possess lipoxygenase inhibiting activity.

1. M. Ferrey, A. Robert, and A. Foucaud, *Synthesis*, 261(1976).
2. F. Duro, *Gazz. Chim. Ital.*, 93, 215(1963); *Chem. Abstr.*, 59, 2793.
3. P. O. Shvaika, V. N. Artemov, S. N. Baranov, *Zh. Org. Khim.*, 1, 1968(1971).
4. T. Matsuda, N. Honjo, M. Yamazaki, and Y. Goto, *Chem. Pharm. Bull.*, 25, 3270(1977).
5. K. Popov-Pergal, M. Pergal, and D. Jeremic, *Bull. Sci. Cons. Acad. Sci. Arts RSF Yougosl.*, Sect. A, 21, 197(1976): *Chem. Abstr.*, 86, 170347m.
6. Fr. Demande FR 2164520, 7 Sep. 1973; *Chem. Abstr.*, 80, 27244w.
7. Ger. Offen. DE 2711330, 22 Sep. 1977; *Chem Abstr.*, 88, 68680.
8. N. Susuki, and T. Goto, *Agr. Biol. Chem.*, 36, 2213 (1972).
9. G. Satzinger, *Justus Liebigs Ann. Chem.* 473(1978).
10. Ger. Offen. DE 2252070, 10 May 1973 to J. A. Edwards, Syntex US Appl. 193, 172. *Chem. Abstr.*, 79, 32036p.
11. E. P. Nesynov, M. M. Besporzvannaya, and P. S. Pel'kis, Khim. Geterotsikl. Soedinenii, 11, 1487 (1973). *Chem. Abstr.*, 80, 82785.
12. S. H. Dandegaonkar and J. B. Patil, *J. Shivaji Univ.*, 1, 159(1974). *Chem. Abstr.*, 86, 106454s.
13. Eur. Pat. Appl. EP 153709A2, 4 Sep. 1985, *Chem. Abstr.*, 104, 148630s.

14. K. T. Potts, K. G. Bordeaux, W. R. Kuehnling, and R. L. Salsbury, *J. Org. Chem.*, 50, 1666(1985).

15. Japanese Patent No. 11256'66; *Chem. Abstr.*, 65, 13716f.

16. H. Behringer and D. Weber, *Annalen*, 682, 201(1965).

17. A. Robert, M. Ferrey, and A. Foucaud, *Tetrahedron Lett.*, 16, 1377(1975).

18. I. V. Smolanka, S. M. Khripak, and V. I. Staninets, *Ukr. Khim. Zh.*, 32 202(1966); *Chem. Abstr.*, 64, 15863.

19. W. Reeve and E. R. Barron, *J. Org. Chem.*, 40, 1917 (1975).

20. P. Chabrier and S. Renard, *Compt. Rend.*, 226, 582 (1948).

21. Belgian Patent No. 623714; *Chem. Abstr.*, 60, 9299.

22. U.S. Pat. No. 3,418,331; *Chem. Abstr.*, 70, 57824.

23. S. C. Mutha and R. Ketcham, *J. Org. Chem.*, 34, 2053 (1969).

24. I. Ito, S. Murakami, and K. Tanabe, *Yakugaku Zasshi*, 86, 300(1966); *Chem. Abstr.*, 65, 3852F.

25. German Patent No. 2611089; *Chem. Abstr.*, 86, 43693.

26. Hungarian Patent Nos. 133776, 133971, and 133972; *Chem. Abstr.*, 43, 3851.

27. R. Bally, *Acta. Crystallogr.*, B29, 2635(1973).

28. French Patent No. 2164520; *Chem. Abstr.*, 80, 27244.

29. German Patent No. 2064307; *Chem. Abstr.*, 77, 101576.

30. J. Metzger, H. Larive, R. Dennilauler, R. Baralle, and C. Gaurat, *Bull. Soc. Chim. France*, 11, 2857(1964); *Chem. Abstr.*, 62, 9263.

31. U.S. Pat. No. 3,850,947; *Chem. Abstr.*, 82, 72978.

32. C. Broquet and A. Tohoukarine, *Compt. Rend.*, C-262, 1017(1966); *Chem. Abstr.*, 64, 19590.

33. German Patent No. 2413937. *Chem. Abstr.*, 82, 4239.

34. K. T. Potts, J. Baum, s. Datta and E. Houghton, *J. Org. Chem.*, 41, 813(1976).

35. U.S. Pat. No. 3,438,992; *Chem. Abstr.*, 71, 61386.

36. K. A. Jensen and I. Crossland, *Acta. Chem. Scand.*, 17, 144(1963).

37. French Patent No. 2067436; *Chem. Abstr.*, 77, 5473.

38. Ger. Offen. DE 2541720, 8 Apr. 1976; *Chem. Abstr.*, 85, 78112n.

39. Eur. Pat. Appl. EP 97323 A2, 4 Jan. 1984; *Chem. Abstr.*, 100, 139093j.

40. Fr. Demande FR 2045672, 9 Apr. 1971; *Chem. Abstr.*, 76, 3860k.

41. Fr. FR 2046114, 5 Mar. 1971; *Chem. Abstr.*, 75, 151800k.

42. Fr. FR 1449800, 19 Aug. 1966; *Chem. Abstr.*, 66, 105907s.

43. Jpn. Kokai Tokkyo Koho JP 61/171480 A2 [86/171480], 2 Aug. 1986; *Chem. Abstr.*, 106, 5019e.

44. Fr. FR 1604530, 7 Jan. 1972; *Chem. Abstr.*, 79, 32038r.

45. Ger. Offen. DE 1915564, 13 Nov. 1969; *Chem. Abstr.*, 72, 68226v.

46. U.S. Pat. No. 4,208,327, 17 Jun. 1980; *Chem. Abstr.*, 94, 30804y.

47. S. H. Dandegaonkar and J. B. Patil, *J. Shivaji Univ.*, 7, 159(1974); *Chem. Abstr.*, 86, 106454s.

48. I. Kopka, *Tetrahedron Lett.*, 29, 3765 (1988).

SYNTHESIS OF THE COMPOUNDS OF THE INVENTION

The 4-hydroxythiazole compounds of this invention can be prepared by reaction schemes I–III below. While more than one reaction scheme may be used to make many of the 4-hydroxythiazole compounds of this invention, the examples are grouped according to the preferred synthetic scheme. The compounds produced by the examples following Scheme I are preferably made according to Scheme I and so on.

4-Hydroxythiazoles of general Formula I may be prepared by the reaction sequence outlined in Scheme I. The meanings of $R_1$ and $R_2$ correspond to the definitions provided above. The reaction of nitriles with alpha-mercaptoacetic acid derivatives at high temperature for several hours provides the 4-hydroxythiazoles. Where groups $R_1$ and $R_2$ contain functionality which would ordinarily interfere with the desired reaction to form the thiazole system, conventional procedures to block the potentially interfering functionality followed by deblocking after thiazole formation may be utilized by those skilled in the art.

Scheme I

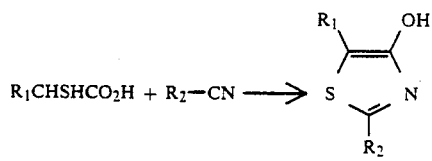

$R_1CHSHCO_2H + R_2-CN \longrightarrow$

EXAMPLE 1

2-(2-Pyridyl)-4-hydroxy-5-methylthiazole

Pyridine (2 g, 0.025 mol) was added to a mixture of thiolactic acid (10.6 g, 0.1 mol) and 2-cyanopyridine (10.4 g, 0.1 mol) at 23° C. under an argon atmosphere. The reaction mixture was then heated at 100° C. and maintained for 2 hours. After cooling, the precipitate was collected and washed with absolute ethanol. Recrystallization from methanol afforded the product (14 g, 73%).

mp 230° C. (MeOH).

$^1$H NMR (60 MHz, DMSO-$d_6$); delta 2.25 (s, 3H), 7.32–7.67 (m, 1H), 8.00–8.30 (m, 1H), 8.54–8.70 (m, 1H), 8.98–9.10 (m, 1H), 10.55 (s, 1H).

Mass Spectrum: 192 (M+).

Annal. Calc'd. for $C_9H_8N_2OS$: C, 56.25; H, 4.17; N, 14.58. Found: C, 56.26; H, 4.18; N, 14.77.

EXAMPLE 2

2-(3-Pyridyl)-4-hydroxy-5-methylthiazole

The title compound was prepared according to the method of Scheme I in a manner analogous to Example 1 except 3-cyanopyridine was used instead of 2-cyanopyridine.

mp 201°–202° C. (MeOH).

$^1$H NMR (60 MHz, DMSO-$d_6$): delta 2.25 (s, 3H), 7.35–7.62 (m, 24), 8.05–8.35 (m, 2H), 10.45 (s, 1H).

Mass Spectrum: 192 (M+).

Anal. Calc'd. for $C_9H_8N_2OS$: C, 56.25; H, 4.17; N, 14.58. Found: C, 56.09; H, 4.17; N, 14.39.

EXAMPLE 3

2-(4-Pyridyl)-4-hydroxy-5-methylthiazole

The title compound was prepared according to the method of Scheme I in a manner analogous to Example 1 except 4-cyanopyridine was used instead of 2-cyanopyridine.

mp 223°-224° C. (EtOH).

$^1$H NMR (60 MHz, DMSO-d$_6$): delta 2.28 (s, 3H), 7.67-7.84 (m, 2H), 8.67-8.85 (m, 2H), 10.65 (s, 1H).

Mass Spectrum: 192 (M+).

Anal. Calc'd. for $C_9H_8N_2OS$: C, 56.25; H, 4.17; N, 14.58. Found: C, 56.37; H, 4.19; N, 14.33.

EXAMPLE 4

2-(3-Quinolinyl)-4-hydroxy-5-methylthiazole

The title compound was prepared according to the method of Scheme I in a manner analogous to Example 1 except 3-quinolinecarbonitrile was used instead of 2-cyanopyridine.

mp 279°-280° C. (EtOH).

$^1$H NMR (300 MHz, DMSO-d$_6$): delta 2.28 (s, 3H), 7.75-7.82 (m, 1H), 7.60-7.68 (m, 1H), 8.02-8.06 (s, 1H), 8.10-8.15 (m, 1H), 8.69-8.72 (m, 1H) 9.32-9.35 (m, 1H), 10.55 (s, 1H).

Mass Spectrum: 242 (M+).

Anal. Calc'd. for $C_{13}H_{10}N_2O_5$: C, 64.46; H, 4.13; N, 11.57. Found: C, 64.76; H, 4.13; N, 11.48.

EXAMPLE 5

2-(2-Furyl)-4-hydroxy-5-methylthiazole

The title compound was prepared according to the method of Scheme I in a manner analogous to Example 1 except 2-cyanofuran was used instead of 2-cyanopyridine.

mp 173°-174° C. (EtOH).

$^1$H NMR (300 MHz, DMSO-d$_6$): delta 2.21 (s, 3H), 6.64-6.68 (m, 1H), 6.86-6.89 (m, 1H), 7.78-7.82 (m, 1H), 10.46 (s, 1H).

Mass Spectrum: 181 (M+)

Anal. Calc'd. for $C_8H_7NO_2S$: C, 53.03; H, 3.87; N, 7.73. Found: C, 53.13; H, 3.88; N, 7.63.

EXAMPLE 6

2-[2-(6-Methoxybenzothiazolyl)]-4-hydroxy-5-methylthiazole

The title compound was prepared according to the method of Scheme I in a manner analogous to Example I except 2-cyano 6-methoxybenzothiazole was used instead of 2-cyanopyridine.

mp 249°-250° C. (EtOH).

$^1$H NMR (300 MHz, DMSO-d$_6$): delta 2.28 (s, 3H), 3.86 (s, 3H), 7.11-7.17 (m, 1H), 7.68-7.72 (m, 1H), 7.90-7.96 (m, 1H), 10.11 (s, 1H).

Mass Spectrum: 278 (M+).

Anal. Calc'd. for $C_{12}H_{10}N_2O_2S_2$: C, 51.80; H, 3.60; N, 10.07. Found: C, 51.65; H, 3.60; N, 10.27.

EXAMPLE 7

2-(2-Thienyl)-4-hydroxy-5-methylthiazole

The title compound was prepared according to the method of Scheme I in a manner analogous to Example 1 except 2-thiophenecarbonitrile was used instead of 2-cyanopyridine.

mp 152°-153° C. (EtOH).

$^1$H NMR (60 MHz, DMSO-d$_6$): delta 2.16 (s, 3H), 7.08-7.28 (m, 1H), 7.50-7.75 (m, 2H), 10.32 (s, 1H).

Mass Spectrum: 197 (M+).

Anal. Calc'd. for $C_8H_7NOS_2$: C, 48.73; H, 3.55; N, 7.11. Found: C, 48.62; H, 3.56; N, 7.24.

EXAMPLE 8

2-(4-Pyrazolyl)-4-hydroxy-5-methylthiazole

The title compound was prepared according to the method of Scheme I in a manner analogous to Example 1 except 4-cyanopyrazole was used instead of 2-cyanopyridine.

mp 124°-125° C. (EtOH).

$^1$H NMR (60 MHz, DMSO-d$_6$): delta 2.16 (s, 3H), 8.00 (s, 1H) 8.35 (s, 1H) 9.02 (s, 1H).

Mass Spectrum: 181 (M+).

Anal. Calc'd. for $C_7H_7N_3OS$: C, 46.41; H, 3.87; N, 23.20. Found: C, 46.32; H, 3.87; N, 23.35.

EXAMPLE 9

2-(4-Fluorophenyl)-4-hydroxy-5-methylthiazole

The title compound was prepared according to the method of Scheme I in a manner analogous to Example 1 except 4-fluorobenzonitrile was used instead of 2-cyanopyridine.

mp 173°-174° C. (EtOH).

$^1$H NMR (60 MHz, DMSO-d$_6$): delta 2.20 (s, 3H), 7.16-8.00 (m, 4H), 10.0 (s, 1H).

Mass Spectrum: 209 (M+)

Anal. Calc'd. for $C_{10}H_8FNOS$: C, 57.42; H, 3.83; N, 6.70. Found: C, 57.30; H, 3.84; N, 6.72.

EXAMPLE 10

2-(4-Bromophenyl)-4-hydroxy-5-methylthiazole

The title compound was prepared according to the method of Scheme I in a manner analogous to Example 1 except 4-bromobenzonitrile was used instead of 2-cyanopyridine.

mp 206°-207° C. (EtOH).

$^1$H NMR (60 MHz, DMSO-d$_6$): delta 2.25 (s, 3H), 7.50-7.90 (m, 4H), 10.32 (s, 1H).

Mass Spectrum: 269 (M+).

Anal. Calc'd. for $C_{10}H_8BrNOS$: C, 44.61; H, 2.97; N, 5.20. Found: C, 44.38; H, 2.99; N, 5.32.

EXAMPLE 11

2-(4-Chlorophenyl)-4-hydroxy-5-methylthiazole

The title compound was prepared according to the method of Scheme I in a manner analogous to Example 1 except 4-chlorobenzonitrile was used instead of 2-cyanopyridine.

mp 198°-199° C. (EtOH).

$^1$H NMR (300 MHz, DMSO-d$_6$): delta 2.23 (s, 3H), 7.48-7.54 (m, 2H), 7.75-7.83 (m, 2H), 10.40 (br s, 1H).

Mass Spectrum: 225 (M+).

Anal. Calc'd. for $C_{10}H_8ClNOS$: C, 53.93; H, 3.60; N, 6.21. Found: C, 54.06; H, 3.62; N, 6.22.

EXAMPLE 12

2-(4-Nitrophenyl)-4-hydroxy-5-methylthiazole

The title compound was prepared according to the method of Scheme I in a manner analogous to Example 1 except 4-nitrobenzonitrile was used instead of 2-cyanopyridine.

mp 244°-248° C. (EtOH).

$^1$H NMR (60 MHz, DMSO-d$_6$) 10.41 (br s, 1H).

Mass Spectrum: 236 (M+).
Anal. Calc'd. for $C_{10}H_8N_2O_3S$: C, 50.85; H, 3.39; N, 11.86. Found: C, 50.78; H, 3.41; N, 11.77.

EXAMPLE 13

2-(4-Carbo-2-phenethoxyphenyl)-4-hydroxy-5-methylthiazole

The title compound was prepared according to the method of Scheme I in a manner analogous to Example 1 except 4-(carbo-2-phenethoxy) benzonitrile was used instead of 2-cyanopyridine.

mp 251°–252° C. (EtOH).
$^1$H NMR (60 MHz, DMSO-$d_6$): delta 2.25 (s, 3H), 3.08 (t, 2H, J=7 Hz), 4.55 (t, 2H J=7 Hz), 7.32–7.50 (m, 5H), 7.95–8.05 (m, 4H), 10.35 (br s, 1H).
Mass Spectrum: 339 (M+).
Anal. Calc'd. for $C_{19}H_{17}NO_3S$: C, 67.24; H, 5.05; N, 4.13. Found: C, 67.00; H, 4.99; N, 4.00.

EXAMPLE 14

2-(4-Benzamido)-4-hydroxy-5-methylthiazole

The title compound was prepared according to the method of Scheme I in a manner analogous to Example 1 except 4-cyanobenzamide was used instead of 2-cyanopyridine.

mp 274°–277° C. (dec.) (EtOH).
$^1$H NMR (60 MHz, DMSO-$d_6$): delta 2.21 (s, 3H), 7.30–8.10 (m, 5H), 10.15 (br s, 1H)
Mass Spectrum: 234 (M+).
Anal. Calc'd. for $C_{11}H_{10}N_2O_2S$: C, 56.40; H, 4.30; N, 11.96. Found: C, 56.37; H, 4.33; N, 11.81.

EXAMPLE 15

2-(4-Biphenyl)-4-hydroxy-5-methylthiazole

The title compound was prepared according to the method of Scheme I in a manner analogous to Example 1 except 4-biphenylcarbonitrile was used instead of 2-cyanopyridine.

mp 265°–266° C. (EtOH).
$^1$H NMR (60 MHz, DMSO, $d_6$): delta 2.16 (s, 3H), 7.32–8.00 (m, 9H), 10.25 (s, 1H).
Mass Spectrum: 267 (M+).
Anal. Calc'd. for $C_{16}H_{13}NOS$: C, 71.91; H, 4.87; N, 5.24. Found: C, 72.12; H, 4.87; N, 5.36.

EXAMPLE 16

2-(4-Trifluoromethylphenyl)-4-hydroxy-5-methylthiazole

The title compound was prepared according to the method of Scheme I in a manner analogous to Example 1 except 4-trifluoromethylbenzonitrile was used instead of 2-cyanopyridine.

mp 232°–233° C. (EtOH).
$^1$H NMR (60 MHz, DMSO-$d_6$): delta 2.20 (s, 3H), 7.66–8.10 (m, 4H), 10.50 (s, 1H).
Mass Spectrum: 259 (M+).
Anal. Calc'd. for $C_{11}H_8F_3NOS$: C, 50.96; H, 3.09; N, 5.41. Found: C, 50.77; H, 3.08; N, 5.27.

EXAMPLE 17

2-(4-Carbomethoxyphenyl)-4-hydroxy-5-methylthiazole

The title compound was prepared according to the method of Scheme I in a manner analogous to Example 1 except methyl 4-cyanobenzoate was used instead of 2-cyanopyridine.

mp 219°–220° C. (EtOH).
$^1$H NMR (60 MHz, DMSO-$d_6$): delta 2.35 (s, 3H), 3.80 (s, 3H), 7.85–8.15 (m, 4H), 10.41 (br s, 1H).
Mass Spectrum: 249 (M+).
Anal. Calc'd. for $C_{12}H_{11}NO_3S$: C, 57.83; H, 4.42; N, 5.62. Found: C, 57.95; H, 4.39; N, 5.49.

EXAMPLE 18

2-(4-Acetylphenyl)-4-hydroxy-5-methylthiazole

The title compound was prepared according to the method of Scheme I in a manner analogous to Example 1 except 4-acetylbenzonitrile was used instead of 2-cyanopyridine.

mp 219°–220° C. (EtOH).
$^1$H NMR (60 MHz, DMSO-$d_6$): delta 2.25 (s, 3H), 2.59 (s, 3H), 7.89–7.95 (m, 2H), 8.0–8.06 (m, 2H), 10.50 (s, 1H).
Mass Spectrum: 233 (M+).
Anal. Calc'd. for $C_{12}H_{11}NO_2S$: C, 61.86; H, 4.72; N, 9.72. Found: C, 61.80; H, 4.72; N, 9.80.

EXAMPLE 19

2-(4-Carboxyphenyl)-4-hydroxy-5-methylthiazole

The title compound was prepared according to the method of Scheme I in a manner analogous to Example 1 except 4-carboxybenzonitrile was used instead of 2-cyanopyridine.

mp 276° C. dec. (EtOH).
$^1$H NMR (300 MHz, DMSO-$d_6$): delta 2.25 (s, 3H), 7.88–7.94 (m, 2H), 7.98–8.04 (m, 2H), 10.49 (br s, 1H), 12.07 (br s, 1H).
Mass Spectrum: 235 (M+).
Anal. Calc'd. for $C_{11}H_9NO_3S$: C, 56.17; H, 3.83; N, 5.96. Found: C, 56.29; H, 3.83; N, 5.88.

EXAMPLE 20

2-(4-Cyanophenyl)-4-hydroxy-5-methylthiazole

The title compound was prepared according to the method of Scheme I in a manner analogous to Example 1 except 4-cyanobenzonitrile was used instead of 2-cyanopyridine.

mp 220°–221° C. (EtOH).
$^1$H NMR (60 MHz, DMSO-$d_6$): delta 2.26 (s, 3H), 7.85–8.10 (m, 4H), 10.55 (br s, 1H).
Mass Spectrum: 216 (M+).
Anal. Calc'd. for $C_{11}H_8N_2OS$: C, 61.11; H, 3.70; N, 12.96. Found: C, 61.22; H, 3.72; N, 12.82.

EXAMPLE 21

2-(4-Thiobenzamido)-4-hydroxy-5-methylthiazole

The title compound was prepared according to the method of Scheme I in a manner analogous to Example 1 except 4-cyanothiobenzamide was used instead of 2-cyanopyridine.

mp 256°–257° C. (EtOH).
$^1$H NMR (60 MHz, DMSO-$d_6$): delta 2.20 (s, 3H), 6.65 (s, 2H), 7.32–7.66 (m, 2H), 7.85–8.10 (m, 2H).
Mass Spectrum: 270 (M+).
Anal. Calc'd. for $C_{10}H_{10}N_2O_3S_2$: C, 44.44; H, 3.70; N, 10.37. Found: C, 44.27; H, 3.73; N, 10.42.

EXAMPLE 22

2-(4-Thiotrifluoromethylphenyl)-4-hydroxy-5-methylthiazole

The title compound was prepared according to the method of Scheme I in a manner analogous to Example 1 except 4-thiotrifluoromethylbenzonitrile was used instead of 2-cyanopyridine.

mp 178°–179° C. (EtOH).

$^1$H NMR (60 MHz, DMSO-$d_6$): delta 2.18 (s, 3H), 3.32 (br s, 1H), 7.66–8.05 (m, 4H), 9.75 (br s, 1H).

Mass Spectrum: 291 (M+).

Anal. Calc'd. for $C_{11}H_8F_3NOS_2$: C, 45.36; H, 2.75; N, 4.81. Found: C, 45.26; H, 2.74; N, 4.79.

EXAMPLE 23

2-(4-Carboethoxyphenyl)-4-hydroxy-5-methylthiazole

The title compound was prepared according to the method of Scheme I in a manner analogous to Example 1 except 4-carboethoxybenzonitrile was used instead of 2-cyanopyridine.

mp 207°–208° C. (EtOH).

$^1$H NMR (60 MHz, DMSO-$d_6$): delta 1.25 (t, 3H, J=7 Hz), 2.35 (s, 3H), 4.32 (q, 2H, J=7 Hz), 7.85–8.15 (m, 4H), 10.41 (br s, 1H).

Mass Spectrum: 263 (M+).

Anal. Calc'd. for $C_{13}H_{13}NO_3S$: C, 59.32; H, 4.94; N, 5.32. Found: C, 59.27; H, 4.96; N, 5.29.

EXAMPLE 24

2-(2-Fluorophenyl)-4-hydroxy-5-methylthiazole

The title compound was prepared according to the method of Scheme I in a manner analogous to Example 1 except 2-fluorobenzonitrile was used instead of 2-cyanopyridine.

mp 159°–160° C.(EtOH).

$^1$H NMR (300 MHz, DMSO-$d_6$): delta 2.25 (s, 3H), 7.30–7.51 (m, 4H), 8.05–8.15 (m, 1H), 10.43 (br s, 1H).

Mass Spectrum: 209 (M+).

Anal. Calc'd. for $C_{10}H_8FNOS$: C, 57.42; H, 3.83; N, 6.70. Found: C, 57.29; H, 3.81; N, 6.68.

EXAMPLE 25

2-(3-Fluorophenyl)-4-hydroxy-5-methylthiazole

The title compound was prepared according to the method of Scheme I in a manner analogous to Example 1 except 3-fluorobenzonitrile was used instead of 2-cyanopyridine.

mp 162°–163° C. (EtOH).

$^1$H NMR (300 MHz, DMSO-$d_6$): delta 2.25 (s, 3H), 7.23–7.31 (m, 1H), 7.48–7.66 (m, 3H), 10.45 (s, 1H).

Mass Spectrum: 209 (M+)

Anal. Calc'd. for $C_{10}H_8FNOS$: C, 57.42; H, 3.83; N, 6.70. Found: C, 57.48; H, 3.84; N, 6.72.

EXAMPLE 26

2-(3-Bromophenyl)-4-hydroxy-5-methylthiazole

The title compound was prepared according to the method of Scheme I in a manner analogous to Example 1 except 3-bromobenzonitrile was used instead of 2-cyanopyridine.

mp 148°–149° C. (EtOH).

$^1$H NMR (60 MHz, DMSO-$d_6$): delta 2.21 (s, 3H), 7.32–8.02 (m, 4H), 10.35 (s, 1H).

Mass Spectrum: 269 (M+).

Anal. Calc'd. for $C_{10}H_8BrNOS$: C, 44.61; H, 2.97; N, 5.20. Found: C, 44.60; H, 2.98; N, 5.25.

EXAMPLE 27

2-(3,5-bis-trifluoromethylphenyl)-4-hydroxy-5-methylthiazole

The title compound was prepared according to the method of Scheme I in a manner analogous to Example 1 except 3,5-bis-trifluoromethylbenzonitrile was used instead of 2-cyanopyridine.

mp 182°–183° C. (EtOH).

$^1$H NMR (300 MHz, DMSO-$d_6$): delta 2.29 (s, 3H), 8.12 (s, 1H), 8.30 (s, 2H), 10.65 (s, 1H).

Mass Spectrum: 327 (M+).

Anal. Calc'd. for $C_{12}H_7F_6NOS$: C, 44.04; H, 2.14; N, 4.28. Found: C, 44.23; H, 2.16; N, 4.31.

EXAMPLE 28

2-(3,5-Dinitrophenyl)-4-hydroxy-5-methylthiazole

The title compound was prepared according to the method of Scheme I in a manner analogous to example 1 except 3,5-dinitrobenzonitrile was used instead of 2-cyanopyridine.

mp 247°–248° C. (EtOH).

$^1$H NMR (60 MHz, DMSO-$d_6$): delta 2.21 (s, 3H), 8.65 (s, 3H), 9.45 (br s, 1H).

Mass Spectrum: 281 (M+).

Anal. Calc'd. for $C_{10}H_7N_3O_5S$: C, 42.70; H, 2.49; N, 14.95. Found: C, 42.62; H, 2.48; N, 14.82.

EXAMPLE 29

2-(2-Chloro-3-methylphenyl)-4-hydroxy-5-methylthiazole

The title compound was prepared according to the method of Scheme I in a manner analogous to Example 1 except 2-chloro-3-methylbenzonitrile was used instead of 2-cyanopyridine.

mp 183°–184° C. (EtOH).

$^1$H NMR (60 MHz, DMSO-$d_6$): delta 2.20 (s, 3H), 2.35 (s, 3H), 7-407-86 (m, 3H), 10.32 (s, 1H).

Mass Spectrum: 239 (M+).

Anal. Calc'd. for $C_{11}H_{10}ClNOS$: C, 55.11; H, 4.84; N, 5.85. Found: C, 55.31; H, 4.86; N, 5.86.

EXAMPLE 30

2-(4-Carboxyphenyl)-4-hydroxy-5-phenylthiazole

The title compound was prepared according to the method of Scheme I in a manner analogous to Example 1 except thiomandelic acid and 4-cyanobenzoic acid were used instead of thiolactic acid and 2-cyanopyridine respectively.

mp 300° C. dec. (EtOH).

$^1$H NMR (60 MHz, DMSO-$d_6$): delta 7.32–8.15 (m, 9H), 11.32 (br s, 1H).

Mass Spectrum: 297 (M+).

Anal. Calc'd. for $C_{16}H_{11}NO_3S$: C, 64.65; H, 3.70; N, 4.71. Found: C, 64.74; H, 3.71; N, 4.58.

4-Hydroxythiazoles of general Formula I are also prepared by the reaction sequence outlined in Scheme II. The meanings of $R_1$ and $R_2$ correspond to the definitions provided above. The reaction of an alpha-haloester with an appropriately substituted thioamide in toluene at high temperature for several hours provides the 4-hydroxythiazoles. Where groups $R_1$ and $R_2$ contain functionality which would ordinarily interfere with the desired reaction to form the thiazole system, conventional procedures to block the potentially interfer-

Scheme II

R₁CHBrCO₂CH₃ + R₂—CSNH₂ ⟶ 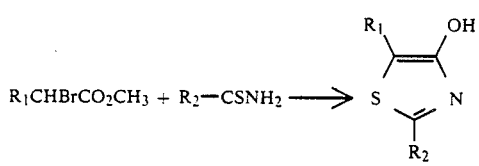

EXAMPLE 31

2-Phenyl-4-hydroxy-5-methylthiazole

Ethyl bromopropionate (3.96 g, 21.87 mmol) was added dropwise to a solution of thiobenzamide (3.00 g, 21.87 mM) and pyridine (7 ml, 87.48 mmol) in toluene (200 ml) at 23° C. The reaction mixture was heated to 80° C. and maintained for 2 hours and allowed to cool to 23° C. The precipitate was collected and recrystallized from ethanol to afford 3.3 g (31%) of product.

mp 192°–193° C. (EtOH).

$^1$H NMR (300 MHz, DMSO-$d_6$): delta 2.20 (s, 3H), 7.32–7.55 (m, 3H), 7.75–7.82 (m, 2H), 10.31 (s, 1H).

Mass Spectrum: 191 (M+).

Anal. Calc'd for $C_{10}H_9NOS$: C, 62.83; H, 4.71; N, 7.33. Found: C, 62.92; H, 4.71; N, 7.18.

EXAMPLE 32

2-(4-Methoxyphenyl)-4-hydroxy-5-methylthiazole

The title compound was prepared according to the method of Scheme II in a manner analogous to Example 31 except 4-methoxythiobenzamide was used instead of thiobenzamide.

mp 149°–150.5° C. (EtOH).

$^1$H NMR (300 MHz, DMSO-$d_6$): delta 2.18 (s, 3H), 7.0–7.20 (m, 2H), 7.67–7.97 (m, 2H), 10.41 (br s, 1H).

Mass Spectrum: 221 (M+).

Anal. Calc'd for $C_{11}H_{11}NO_2S$: C, 59.72; H, 4.97; N, 6.33. Found: C, 59.86; H, 4.99; N, 6.22.

EXAMPLE 33

2-(4-Methylphenyl)-4-hydroxy-5-methylthiazole

The title compound was prepared according to the method of Scheme II in a manner analogous to Example 31 except 4-methylthiobenzamide was used instead of thiobenzamide.

mp 172°–174° C. (EtOH).

$^1$H NMR (60 MHz, DMSO-$d_6$): delta 2.15 (s, 3H), 2.25 (s, 3H), 7.15–7.35 (m, 2H), 7.55–7.85 (m, 2H), 9.82 (s, 1H).

Mass Spectrum: 205 (M+).

Anal. Calc'd for $C_{11}H_{11}NOS$: C, 64.36; H, 5.40; N, 6.82. Found: C, 64.15; H, 5.38; N, 6.71.

EXAMPLE 34

2-Phenyl-4-hydroxy-5-phenylthiazole

The title compound was prepared according to the method of Scheme II in a manner analogous to Example 31 except chlorophenylacetylchloride was used instead of ethyl 2-bromopropionate.

mp 212°–213° C. (EtOH).

$^1$H NMR (300 MHz, CDCl₃): delta 7.22–7.30 (m, 2H), 7.38–7.53 (m, 4H), 7.82–7.87 (m, 2H), 7.92–8.00 (m, 2H).

Mass Spectrum: 253 (M+).

Anal. Calc'd for $C_{15}H_{11}NOS$: C, 71.15; H, 4.35; N, 5.53. Found: C, 71.22; H, 4.33; N, 5.44.

EXAMPLE 35

2-Phenyl-4-hydroxy-5-ethylthiazole

The title compound was prepared according to the method of Scheme II in a manner analogous to Example 31 except methyl 2-bromobutyrate was used instead of ethyl 2-bromopropionate.

mp 175°–177° C. dec. (MeOH).

$^1$H NMR (300 MHz, DMSO-$d_6$): delta 1.18 (t, 3H, J=7 Hz), 2.66 (q, 2H, J=7 Hz), 7.40–7.50 (m, 3H), 7.75–7.85 (m, 2H), 9.52 (br s, 1H).

Mass Spectrum: 205 (M+).

Anal. Calc'd for $C_{11}H_{11}NOS$: C, 64.39; H, 5.36; N, 6.83. Found: C, 64.28; H, 5.38; N, 6.97.

EXAMPLE 36

2-Phenyl-4-hydroxy-5-propylthiazole

The title compound was prepared according to the method of Scheme II in a manner analogous to Example 31 except ethyl 2-bromovalerate was used instead of ethyl 2-bromopropionate.

mp 86°–87° C. (EtOH).

$^1$H NMR (300 MHz, DMSO-$d_6$): delta 0.92 (t, 3H, J=7 Hz), 1.50–1.65 (m, 2H), 2.62 (t, 2H, J=7 Hz), 7.35–7.55 (m, 3H), 7.75–7.83 (m, 2H), 10.28 (s, 1H).

Mass Spectrum: 219 (M+).

Anal. Calc'd for $C_{12}H_{13}NOS$: C, 65.75; H, 5.94; N, 6.39. Found: C, 65.71; H, 5.95; N, 6.41.

EXAMPLE 37

2-Phenyl-4-hydroxy-5-butylthiazole

The title compound was prepared according to the method of Scheme II in a manner analogous to Example 31 except ethyl 2-bromohexanoate was used instead of ethyl 2-bromopropionate.

mp 69°–71° C. (EtOH).

$^1$H NMR (300 MHz, DMSO-$d_6$): delta 0.90 (t, 3H, J=7 Hz), 1.28–1.41 (m, 2H), 1.48–1.60 (m, 2H), 2.63 (t, 2H, J=7 Hz), 7.40–7.50 (m, 3H), 7.82–7.85 (m, 2H), 10.35 (s, 1H).

Mass Spectrum: 233 (M+)

Anal. Calc'd for $C_{13}H_{15}NOS$: C, 66.92; H, 6.48; N, 6.00. Found: C, 66.32; H, 6.47; N, 5.83.

EXAMPLE 38

2-Phenyl-4-hydroxy-5-phenethylthiazole

The title compound was prepared according to the method of Scheme II in a manner analogous to Example 31 except ethyl 3-phenyl-2-bromobutyrate was used instead of ethyl 2-bromopropionate.

mp 127°–128° C. (EtOH).

$^1$H NMR (60 MHz, DMSO-$d_6$): delta 2.88 (s 4H), 7.21–7.90 (m, 10H), 9.84 (br s, 1H).

Mass Spectrum: 281(M+).

Anal. Calc'd for $C_{17}H_{15}NOS$: C, 72.60; H, 5.34; N, 4.98. Found: C, 72.66; H, 5.35; N, 4.97.

EXAMPLE 39

2-Phenyl-4-hydroxy-5-(methylcarbomethoxy)-thiazole

The title compound was prepared according to the method of Scheme II in a manner analogous to Example 31 except ethyl bromosuccinate was used instead of ethyl 2-bromopropionate.

mp 114°–116° C. (EtOH).

ing functionality followed by deblocking after thiazole formation may be utilized by those skilled in the art.

¹H NMR (300 MHz, DMSO-d₆): delta 3.65 (s, 2H), 3.80 (s, 3H), 7.35–7.55 (m, 3H), 7.72–7.39 (m, 2H), 10.50 (s, 1H).

Mass Spectrum: 249 (M+).

Anal. Calc'd for $C_{12}H_{11}NO_3S$: C, 57.83; H, 4.42; N, 5.62. Found: C, 57.90; H, 4.42; N, 5.64.

EXAMPLE 40

2-Phenyl-4-hydroxy-5-methylhydroxyaminocarbonyl-methylthiazole

The title compound was prepared from the acid chloride of Example 39 using methylhydroxylamine.

mp 156°–157° C. (Ether).

¹H NMR (300 MHz, DMSO-d₆): delta 3.12 (s, 3H), 3.80 (s, 2H), 7.38–7.52 (m, 3H), 7.75–7.86 (m, 2H), 10.10 (br s, 1H), 10.51 (s, 1H).

Mass Spectrum: 264 (M+).

Anal. Calc'd for $C_{12}H_{12}N_2O_3S$: C, 54.54; H, 4.55; N, 10.61. Found: C, 54.28; H, 4.55; N, 10.47.

EXAMPLE 41

2-(3-Pyridyl)-4-hydroxy-5-phenylthiazole

The title compound was prepared according to the method of Scheme II in a manner analogous to Example 31 except thioisonicotinamide was used instead of ethyl 2-bromopropionate.

mp 273°–276° C. (EtOH).

¹H NMR (300 MHz, DMSO-d₆): delta 7.20–7.30 (m, 1H), 7.35–7.48 (m 2H), 7.52–7.80 (m, 3H), 8.25–8.40 (m, 1H), 8.63–8.80 (m, 1H), 9.01–9.15 (m, 1H), 10.20 (br s, 1H).

Mass Spectrum: 254 (M+).

Anal. Calc'd for $C_{14}H_{10}N_2OS$: C, 66.14; H, 3.94; N, 11.02. Found: C, 66.32; H, 3.94; N, 11.22.

EXAMPLE 42

2-(4-Pyridyl)-4-hydroxy-5-phenylthiazole

The title compound was prepared according to the method of Scheme II in a manner analogous to Example 31 except 4-thioamidopyridine was used instead of thiobenzamide and 2-chloro-2-phenylacetyl chloride was used instead of 2-bromopropionate.

mp 280° C. dec. (EtOH).

¹H NMR (60 MHz, DMSO-d₆): delta 7.15–7.95 (m,9H), 8.55 (br s,1H).

Mass Spectrum: 254 (M+).

Anal. Calc'd for $C_{14}H_{10}N_2OS$: C, 66.14; H, 3.94; N, 11.02. Found: C, 66.27; H, 3.95; N, 11.18.

EXAMPLE 43

2-(4-Methoxyphenyl)-4-hydroxy-5-phenylthiazole

The title compound was prepared according to the method of Scheme II in a manner analogous to Example 31 except 4-methoxythiobenzamide was used instead of thiobenzamide and 2-chloro-2-phenylacetyl chloride was used instead of 2-bromopropionate.

mp 218°–221° C. (EtOH).

¹H NMR (60 MHz, DMSO-d₆): delta 3.84 (s, 3H), 7.0–8.0 (m 9H), 11.05 (br s, 1H).

Mass Spectrum: 283 (M+).

Anal. Calc'd for $C_{16}H_{13}NO_2S$: C, 67.84; H, 4.95: N, 4.96. Found: C, 67.73; H, 4.96; N, 4.91.

EXAMPLE 44

2-Biphenyl-4-hydroxy-5-phenylthiazole

The title compound was prepared according to the method of Scheme II in a manner analogous to Example 31 except 4-phenylthiobenzamide was used instead of thiobenzamide and 2-chloro-2-phenylacetyl chloride was used instead of 2-bromopropionate.

mp 242°–243° C. (EtOH).

¹H NMR (60 MHz, DMSO-d₆): delta 7.15–8.05 (m, 14H), 11.25 (br s, 1H),

Mass Spectrum: 329 (M+).

Anal. Calc'd for $C_{21}H_{15}NOS$: C, 76.57; H, 4.59; N, 4.25. Found: C, 76.75; H, 4.58; N, 4.08.

EXAMPLE 45

2-Methyl-4-hydroxy-5-phenylthiazole

The title compound was prepared according to the method of Scheme II in a manner analogous to Example 31 except methylthioamide was used instead of thiobenzamide and 2-chloro-2-phenylacetyl chloride was used instead of 2-bromopropionate.

mp 208°–211° C. (EtOH).

¹H NMR (300 MHz, DMSO-d₆): delta 2.56 (s, 3H), 7.13–7.20 (m, 1H), 7.30–7.40 (m 2H), 7.59–7.65 (m, 4H), 8.50 (br s, 1H).

Mass spectrum: 191 (M+).

Anal. Calc'd for $C_{10}H_9NOS$: C, 62.80; H, 4.74; N, 7.32. Found: C, 62.90; H, 4.76; N, 7.41.

EXAMPLE 46

2-(4-Methylphenyl)-4-hydroxy-5-phenylthiazole

The title compound was prepared according to the method of Scheme II in a manner analogous to Example 31 except 4-methylthiobenzamide was used instead of thiobenzamide and 2-chloro-2-phenylacetyl chloride was used instead of 2-bromopropionate.

mp 252°–255° C. (EtOH).

¹H NMR (60 MHz, DMSO-d₆): delta 2.32 (s, 3H), 7.20–7.95 (m,9H), 10.75 (br s, 1H).

Mass Spectrum: 267 (M+).

Anal. Calc'd for $C_{16}H_{13}NOS$: C, 71.88; H, 4.90; N, 5.24. Found: C, 72.01; H, 4.86; N, 5.21.

EXAMPLE 47

2-(4-Fluorophenyl)-4-hydroxy-5-phenylthiazole

The title compound was prepared according to the method of Scheme II in a manner analogous to Example 31 except 4-fluorothiobenzamide was used instead of thiobenzamide and 2-chloro-2-phenylacetyl chloride was used instead of 2-bromopropionate.

mp 231°–233° C. (EtOH).

¹H NMR (60 MHz, DMSO-d₆): delta 7.20–8.05 (m, 9H), 11.10 (br s, 1H).

Mass Spectrum: 271 (M+).

Anal. Calc'd for $C_{15}H_{10}FNOS$: C, 66.41; H, 3.72; N, 5.16. Found: C, 66.61; H, 3.82; N, 5.28.

EXAMPLE 48

2-(4-Ethoxyphenyl)-4-hydroxy-5-phenylthiazole

The title compound was prepared according to the method of Scheme II in a manner analogous to Example 31 except 4-ethoxythiobenzamide was used instead of thiobenzamide and 2-chloro-2-phenylacetyl chloride was used instead of 2-bromopropionate.

mp 214°–216° C. (EtOH).

¹H NMR (60 MHz, DMSO-d₆): delta 1.55 (t, J=7 Hz, 3H), 4.35 (q, J=7 Hz, 2H), 7.15-8.25 (m, 9H), 10.50 (br s, 1H).

Mass Spectrum: 297 (M+).

Anal. Calc'd for $C_{17}H_{15}NO_2S$: C, 68.66; H, 5.37; N, 4.98. Found: C, 68.46; H, 5.27; N, 4.80.

EXAMPLE 49

2-Pentyl-4-hydroxy-5-phenylthiazole

The title compound was prepared according to the method of Scheme II in a manner analogous to Example 31 except thiohexanamide was used instead of thiobenzamide and 2-chloro-2-phenylacetyl chloride was used instead of 2-bromopropionate.

mp 128°-130° C. (Acetone).

¹H NMR (300 MHz, DMSO-d₆): delta 0.88 (t, 3H, J=7 Hz), 1.22-1.40 (m, 4H), 1.65-1.75 (m, 4H), 2.85 (t, 2H, J=7 Hz), 7.10-7.20 (m, 1H), 7.30-7.40 (m, 2H), 7.58-7.65 (m, 2H).

Mass Spectrum: 247 (M+).

Anal. Calc'd for $C_{14}H_{17}NOS$: C, 68.02; H, 6.88; N, 5.66. Found; C, 67.88; H, 6.90; N, 5.69.

4-Hydroxythiazole derivatives of general Formula I may also be prepared directly from the parent 4-hydroxythiazole. In many cases the group R₃ is a metabolically cleavable group. When the group R₃ is removed by metabolic processes, the group R₃ can be substituted with a hydrogen, another group, or a salt which yields an active enzyme inhibitor. Examples of metabolically cleavable groups for R₃ include COR₄ and CONR₅R₆ wherein R₄, R₅ and R₆ are as before defined.

Scheme III

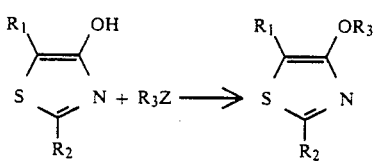

EXAMPLE 50

2-Phenyl-4-acetoxy-5-phenylthiazole

The title compound was prepared by reacting the compound of Example 34 with one equivalent of acetic anhydride and pyridine in methylene chloride at 23° C. for 10 hours.

mp 101°-103° C. (EtOAc/hexane).

¹H NMR (300 MHz, DMSO-d₆): delta 2.40 (s, 3H), 7.38-7.62 (m, 8H), 7.86-7.96 (m, 2H).

Mass Spectrum: 295 (M+).

Anal. Calc'd for $C_{17}H_{13}NO_2S$: C, 69.15; H, 4.40; N, 4.75. Found: C, 69.18; H, 4.41; N, 4.77.

EXAMPLE 51

2-Phenyl-4-hexanoxy-5-phenylthiazole

The title compound was prepared by reacting the compound of Example 34 with one equivalent of hexanoyl chloride in methylene chloride at 23° C. for 5 hours.

mp 70°-72° C. (EtOH).

¹H NMR (300 MHz, CDCl₃): delta 0.90 (t, 3H, J=7 Hz), 1.23-1.40 (m, 4H), 1.65-1.80 (m, 2H), 2.61 (t, 2H, J=7 Hz), 7.28-7.58 (m, 8H), 7.88-7.96 (m, 2H).

Mass Spectrum: 351 (M+).

Anal. Calc'd for $C_{21}H_{21}NO_2S$: C, 71.77; H, 6.02; N, 3.99. Found: C, 71.54; H, 5.95; N, 3.96.

EXAMPLE 52

2-Phenyl-4-trimethylacetoxy-5-phenylthiazole

The title compound was prepared by reacting the compound of Example 34 with one equivalent of pivaloyl chloride and 4-dimethylaminopyridine in methylene chloride at 23° C. for 2 hours.

mp 134°-136° C. (EtOAc/hexane).

¹H NMR (300 MHz, CDCl₃): delta 1.38 (s, 9H), 7.40 (m, 6H), 7.56 (m, 2H), 7.92 (m, 2H).

Mass Spectrum: 337 (M+).

Anal. Calc'd for $C_{20}H_{19}NO_2S$: C, 71.22; H, 5.64; N, 4.15. Found: C, 71.30; H, 5.64; N, 4.14.

EXAMPLE 53

2-Phenyl-4-ethyl succinyloxy-5-phenylthiazole

The title compound was prepared by reacting the compound of Example 34 with one equivalent of ethyl succinyl chloride and 4-dimethylaminopyridine in methylene chloride at 23° C. for 10 hours.

mp 55°-58° C. (EtOAc/hexane).

¹H NMR (300 MHz, CDCl₃): delta 1.25 (g, J=7 Hz, 3H), 2.73 (t, J=7 Hz, 2H), 2.98 (t, J=7 Hz, 2H), 4.15 (q, J=7 Hz, 2H), 7.45 (m, 6H), 7.55 (m, 2H), 7.92 (m, 2H).

Mass Spectrum: 381 (M+).

Anal. Calc'd for $C_{21}H_{19}NO_4S$: C, 66.14; H, 4.99; N, 3.67. Found: C, 66.33; H, 4.99; N, 3.73.

EXAMPLE 54

2-Phenyl-[4-(carboethoxy)oxy]-5-propylthiazole

The title compound was prepared by reacting the compound of Example 36 with one equivalent of ethyl chloroformate and pyridine in toluene at 23° C. for 2 hours to afford a colorless oil.

¹H NMR (300 MHz, CDCl₃): delta 1.00 (t, 3H), J=7 Hz), 1.40 (t, 3H, J=7 Hz), 1.62-1.76 (m, 2H), 2.69 (t, 2H, J=7 Hz), 4.35 (q, 2H, J=7 Hz), 7.40 (m, 3H), 7.87 (m, 2H).

Mass Spectrum: 291 (M+).

Anal. Calc'd for $C_{15}H_{17}NO_3S$: C, 61.83; H, 5.88; N, 4.81. Found: C, 61.78; H, 5.98; N, 4.65.

EXAMPLE 55

2-Phenyl-4-(N-methylcarbamyl)oxy-5-propylthiazole

The title compound was prepared by reacting Example 36 with one equivalent of methyl isocyanate and triethylamine in benzene at 23° C. for 20 hours.

mp 55°-58° C. (toluene).

¹H NMR (60 MHz, CDCl₃): delta 0.90 (t, 3H, J=7 Hz), 1.67 (m, 2H), 2.66 (t, 24, J=7 Hz), 2.85 (d, 3H, J=7 Hz), 5.50 (br s, 1H), 7.75 (m, 2H), 7.40 (m, 3H).

Mass Spectrum: 276 (M+).

Anal. Calc'd for $C_{14}H_{16}N_2O_2S$: C, 60.85; H, 5.84; N, 10.14. Found: C, 60.55; H, 5.85; N, 10.08.

EXAMPLE 56

2-Phenyl-[4-(benzoyl)oxy]-5-propylthiazole

The title compound was prepared by reacting the compound of Example 36 with one equivalent of benzylchloroformate in toluene at 23° C. for 6 hours.

mp 62°-64° C. (toluene).

¹H NMR (60 MHz, DMSO-d₆): delta 7.15-8.05 (m, 14H), 11.25 (br s, 1H).

Mass Spectrum: 329 (M+).

Anal. Calc'd for $C_{21}H_{15}NOS$: C, 76.57; H, 4.59; N, 4.25. Found: C, 76.75; H, 4.58; N, 4.08.

EXAMPLE 57

2-Phenyl-4-(N-t-butylcarbamyl)oxy-5-propylthiazole

The title compound was prepared by reacting the compound of Example 36 with one equivalent of t-butyl isocyanate and triethylamine in benzene at 23° C. for 20 hours.

mp 97°–98° C. (benzene).

$^1$H NMR (300 MHz, CDCl$_3$): delta 0.89 (t, 3H, J=7 Hz), 1.21–1.45 (m, 2H), 0.99 (s, 9H), 2.55 (t, 2H, J=7 Hz), 7.05–7.10 (m, 1H), 7.30–7.60 (m, 4H).

Mass Spectrum: 318 (M+).

Anal. Calc'd for $C_{17}H_{22}N_2O_2S$: C, 64.15; H, 6.92; N, 8.80. Found: C, 64.37; H, 7.01; N, 8.62.

EXAMPLE 58

2-Phenyl-4-(N-phenylcarbamyl)oxy-5-propylthiazole

The title compound was prepared by reacting the compound of Example 36 with one equivalent of phenyl isocyanate in benzene at 23° C. for 20 hours.

mp 104°–105° C. (Ether).

$^1$H NMR (300 MHz, CDCl$_3$): delta 0.99 (t, 3H, J=7 Hz), 1.58–1.63 (m, 2H), 2.61 (t, 2H, J=7 Hz), 7.05–7.16 (m, 1H), 7.30–7.50 (m, 8H), 7.80–7.90 (m, 2H).

Mass Spectrum: 338 (M+).

Anal. Calc'd for $C_{19}H_{18}N_2O_2S$: C, 67.43; H, 5.36; N, 8.28. Found: C, 67.45; H, 5.40; N, 8.28.

EXAMPLE 59

2-Phenyl-4-acetoxy-5-propylthiazole

The title compound was prepared by reacting the compound of Example 36 with one equivalent of acetic anhydride and pyridine in methylene chloride at 23° C. for 10 hours. The product was a colorless oil.

$^1$H NMR (300 MHz, DMSO-d$_6$): delta 0.90 (t, 3H, J=Hz), 1.50–1.65 (m, 2H), 2.28 (s, 3H), 2.62 (t, 2H, J=7 Hz), 7.35–7.55 (m, 3H), 7.75–7.83 (m, 2H).

Mass Spectrum: 261 (M+).

Anal. Calc'd for $C_{14}H_{15}NO_2S$: C, 64.37; H, 5.75; N, 5.36. Found: C, 64.39; H, 5.75; N, 5.39.

EXAMPLE 60

2-(4-Carbomethoxyphenyl)-4-acetoxy-5-methylthiazole

The title compound was prepared by reacting the compound of Example 17 with one equivalent of acetic anhydride and pyridine in methylene chloride at 23° C. for 10 hours.

mp 124°–125° C. (EtOH).

$^1$H NMR (60 MHz, CDCl$_3$): delta 2.40 (s, 3H), 2.32 (s, 3H), 3.90 (s, 3H), 7.84–8.32 (m, 4H).

Mass Spectrum: 291 (M+).

Anal. Calc'd for $C_{14}H_{13}NO_4S$: C, 57.73; H, 4.47; N, 4.81. Found: C, 57.69; H, 4.48; N, 4.83.

EXAMPLE 61

2-[2-(6-Methoxy)benzothiazoyl]-4-acetoxy-5-methylthiazole

The title compound was prepared by reacting the compound of Example 6 with one equivalent of acetic anhydride and pyridine in methylene chloride at 23° C. for 10 hours.

mp 183°–184° C. (EtOH).

$^1$H NMR (60 MHz, CDCl$_3$): delta 2.30 (s, 3H), 2.33 (s, 3H), 3.85 (s, 3H), 7.0–7.5 (m, 2H), 7.80–8.00 (m, 1H).

Mass Spectrum: 320 (M+).

Anal. Calc'd for $C_{14}H_{12}N_2O_3S_2$: C, 52.50; H, 4.27; N, 8.75. Found: C, 52.45; H, 3.75; N, 8.77.

EXAMPLE 62

2-(4-Methylphenyl)-4-acetoxy-5-phenylthiazole

The title compound was prepared by reacting the compound of Example 46 with one equivalent of acetic anhydride and pyridine in methylene chloride at 23° C. for 10 hours.

mp 122°–125° C. (EtOH).

$^1$H NMR (60 MHz, CDCl$_3$): delta 2.20 (s, 3H), 2.30 (s, 3H), 7.20–7.95 (m, 9H).

Mass Spectrum: 267 (M+).

Anal. Calc'd for $C_{18}H_{15}NO_2S$: C, 69.88; H, 4.89; N, 4.53. Found: C, 70.02; H, 4.90; N, 4.27.

EXAMPLE 63

2-(4-Ethoxyphenyl)-4-acetoxy-5-phenyl-thiazole

The title compound was prepared by reacting Example 48 with one equivalent of acetic anhydride and pyridine in methylene chloride at 23° C. for 10 hours.

mp 149°–150° C. (EtOH).

$^1$H NMR (60 MHz, CDCl$_3$): delta 1.50 (t, 3H, J=7 Hz), 2.25 (s, 3H), 4.25 (q, 2H, J=7 Hz), 6.90–7.70 (m, 9H).

Mass Spectrum: 339 (M+).

Anal. Calc'd for $C_{19}H_{17}NO_3S$: C, 67.24; H, 5.05; N, 4.13. Found: C, 67.17; H, 5.03; N, 3.98.

EXAMPLE 64

2-(4-Carbo-2-phenethoxyphenyl)-4-acetoxy-5-methylthiazole

The title compound was prepared by reacting the compound of Example 13 with one equivalent of acetic anhydride and pyridine in methylene chloride at 23° C. for 10 hours.

mp 109°–111° C. (EtOH).

$^1$H NMR (60 MHz, CDCl$_3$): delta 2.10 (s, 3H), 2.20 (s, 3H), 3.05 (t, 2H, J=7 Hz), 4.60 (t, 2H, J=7 Hz), 7.25–7.50 (m, 5H) 7.80–8.15 (m, 4H).

Mass Spectrum: 383 (M+).

Anal. Calc'd for $C_{21}H_{19}NO_4S$: C, 66.12; H, 5.02; N, 3.67. Found: C, 66.27; H, 5.04; N, 3.69.

EXAMPLE 65

2-Biphenyl-4-acetoxy-5-phenylthiazole

The title compound was prepared by reacting the compound of Example 44 with one equivalent of acetic anhydride and pyridine in methylene chloride at 23° C. for 10 hours.

mp 146°–147° C. (EtOH).

$^1$H NMR (60 MHz, CDCl$_3$): delta 2.30 (s, 3H), 7.30–8.05 (m, 14H).

Mass Spectrum: 371 (M+).

Anal. Calc'd for $C_{23}H_{17}NO_2S$: C, 74.37; H, 4.61; N, 3.77. Found: C, 74.16; H, 4.60; N, 3.69.

EXAMPLE 66

2-(4-Carboxyphenyl)-4-acetoxy-5-methylthiazole

The title compound was prepared by reacting the compound of Example 19 with one equivalent of acetic anhydride and two equivalents of pyridine in methylene chloride at 23° C. for 10 hours.

mp 227°–230° C. (EtOH).

$^1$H NMR (60 MHz, CDCl$_3$): delta 2.30 (s, 3H), 2.32 (s, 3H), 7.84–8.20 (m, 4H).

Mass Spectrum: 277 (M+).

Anal. Calc'd for C$_{13}$H$_{11}$NO$_4$S: C, 56.31; H, 4.00; N, 5.05. Found: C, 56.11; H, 4.04; N, 5.03.

EXAMPLE 67

2-Phenyl-4-acetoxy-5-butylthiazole

The title compound was prepared by reacting the compound of Example 37 with one equivalent of acetic anhydride and pyridine in methylene chloride at 23° C. for 10 hours. The product was a colorless oil.

$^1$H NMR (60 MHz, CDCl$_3$): delta 0.85 (t, 3H, J=7 Hz), 1.0–1.65 (m, 4H), 2.20 (s, 3H), 2.55 (t, 2H, J=7 Hz), 7.32–7.50 (m, 3H), 7.80–8.00 (m, 2H).

Mass Spectrum: 275 (M+).

Anal. Calc'd for C$_{15}$H$_{17}$NO$_2$S: C, 65.43; H, 6.22; N, 5.09. Found: C, 65.44; H, 6.18; N, 4.97.

EXAMPLE 68

2-Pentyl-4-acetoxy-5-propylthiazole

The title compound was prepared by reacting the compound of Example 49 with one equivalent of acetic anhydride and pyridine in methylene chloride at 23° C. for 10 hours. The product was a colorless oil.

$^1$H NMR (300 MHz, CDCl$_3$): delta 0.90 (t, 3H, J=7 Hz), 0.95 (t, 3H, J=7 Hz), 1.30–1.41 (m, 4H), 1.54–1.81 (m, 4H), 2.55 (t, 2H, J=7Hz), 2.87 (t, 2H, J=7 Hz), 2.30 (s, 3H).

Mass Spectrum: 255 (M+).

Anal. Calc'd for C$_{13}$H$_{21}$NO$_2$S: C, 61.14; H, 8.29; N, 5.48. Found: C, 60.97; H, 8.24; N, 5.45.

5-Lipoxygenase IC$_{50}$ Determination

The compounds of this invention are potent inhibitors of 5-lipoxygenase. An assay to determine 5-lipoxygenase activity was performed in incubations containing various concentrations of the test compound and the 20,000×g supernatant from 7.5×10$^6$ homogenized RBL-1 cells in a manner similar to that reported by Dyer et al., Fed. Proc., Fed. Am. Soc. Exp. Biol. 1984, 43, 1462A. Reactions were initiated by the addition of radiolabeled arachidonic acid and terminated by acidification and ether extraction. Reaction products were separated from nonconvented substrate by thin layer chromatography and measured by liquid scintillation spectroscopy. Inhibition of 5-lipoxygenase activity was calculated as the ratio of the amounts of product formed in the presence and absence of inhibitor. IC$_{50}$ values were computed as the 50% intercept from linear regression analysis of plots of percentage inhibition versus log concentration of the compound and are shown in Table 3.

TABLE 3

In Vitro Inhibitory Potencies of Compounds of this Invention Against 5-lipoxygenase from RBL-1 20,000 × g Supernatant

| Example | IC$_{50}$ (μM) (95% CL) |
|---|---|
| 6 | 0.89 (0.71–1.1) |
| 9 | 0.35 (0.28–0.43) |
| 10 | 0.51 (0.50–0.51) |
| 11 | 0.57 (0.52–0.63) |
| 13 | 0.98 (0.78–1.30) |
| 17 | 0.88 (0.65–1.1) |
| 18 | 0.90 (0.66–1.2) |
| 20 | 0.70 (0.58–0.83) |
| 23 | 0.71 (0.60–0.85) |
| 24 | 0.50 (0.43–0.59) |
| 25 | 0.66 (0.56–0.76) |
| 26 | 0.48 (0.39–0.63) |
| 29 | 0.82 (0.76–0.89) |
| 31 | 0.96 (0.8–1.1) |
| 33 | 0.63 (0.62–0.64) |
| 34 | 0.53 (0.52–0.55) |
| 35 | 0.83 (0.73–0.92) |
| 36 | 0.58 (0.55–0.62) |
| 38 | 0.69 (0.62–0.78) |
| 53 | 0.75 (0.69–0.80) |
| 54 | 0.91 (0.83–0.99) |
| 60 | 0.69 (0.64–0.73) |
| 67 | 0.95 (0.81–1.1) |
| | % Inhibition at μM Conc. |
| 41 | 83% at 0.3 |
| 43 | 88% at 0.3 |
| 46 | 91% at 0.4 |
| 47 | 82% at 0.4 |
| 48 | 77% at 0.4 |
| 50 | 88% at 0.4 |
| 62 | 93% at 0.5 |
| 65 | 82% at 0.75 |
| 68 | 79% at 1 |

What is claimed is:

1. A compound having the structure:

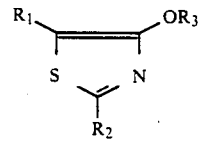

wherein

R$_1$ is unsubstituted phenyl or phenyl substituted with one or more substituents independently selected from the group consisting of halogen, alkyl of from one to twelve carbon atoms, halosubstituted alkyl of from one to twelve carbon atoms, cyano, nitro, COR$_4$, SO$_2$R$_4$, NR$_5$R$_6$ and OR$_6$ wherein R$_4$ at each occurrence is alkyl of from one to twelve carbon atoms, and R$_5$ and R$_6$ are independently hydrogen or alkyl of from one to twelve carbon atoms;

R$_2$ is unsubstituted phenyl or phenyl substituted with one or more substituents independently selected from the group consisting of halogen, alkyl of from one to twelve carbon atoms, halosubstituted alkyl of from one to twelve carbon atoms, cyano, nitro, COR$_4$, SO$_2$R$_4$, NR$_5$R$_6$ and OR$_6$ wherein R$_4$, R$_5$ and R$_6$ are as previously defined; and R$_3$ is hydrogen or a pharmaceutically acceptable salt.

2. A composition for inhibiting lipoxygenase enzyme activity in a mammal in need of such treatment comprising a therapeutically effective amount of a compound as defined by claim 1 in combination with a pharmaceutically acceptable carrier.

3. A method of inhibiting lipoxygenase enzyme activity in a mammal in need of such treatment comprising administering to said mammal a therapeutically effective amount of a compound as defined by claim 1.

* * * * *